United States Patent
Biggadike et al.

(10) Patent No.: US 7,125,985 B2
(45) Date of Patent: Oct. 24, 2006

(54) COMPOUNDS USEFUL IN THE MANUFACTURE OF AN ANTI-INFLAMMATORY ANDROSTANE DERIVATIVE

(75) Inventors: Keith Biggadike, Stevenage (GB); Steven John Coote, Stevenage (GB); Rosalyn Kay Nice, Stevenage (GB)

(73) Assignee: Glaxo Group Limited, Greenford (GB)

( * ) Notice: Subject to any disclaimer, the term of this patent is extended or adjusted under 35 U.S.C. 154(b) by 78 days.

(21) Appl. No.: 10/862,555

(22) Filed: Jun. 7, 2004

(65) Prior Publication Data
US 2004/0224931 A1 Nov. 11, 2004

Related U.S. Application Data

(62) Division of application No. 09/958,050, filed as application No. PCT/GB01/03495 on Aug. 3, 2001.

(30) Foreign Application Priority Data
Aug. 5, 2000 (GB) .................... 0019172.6

(51) Int. Cl.
*C07J 17/00* (2006.01)
(52) U.S. Cl. .................................... 540/114
(58) Field of Classification Search ................. 540/114
See application file for complete search history.

(56) References Cited
U.S. PATENT DOCUMENTS

| | | |
|---|---|---|
| 3,067,197 A | 12/1962 | Agnello et al. |
| 3,639,434 A | 2/1972 | Oxley et al. |
| 3,755,302 A | 8/1973 | Ercoli et al. |
| 3,828,080 A | 8/1974 | May et al. |
| 3,856,828 A | 12/1974 | Phillips et al. |
| 3,981,894 A | 9/1976 | Phillips et al. |
| 3,989,686 A | 11/1976 | Phillips et al. |
| 4,093,721 A | 6/1978 | Phillips et al. |
| 4,187,301 A | 2/1980 | Edwards |
| 4,188,385 A | 2/1980 | Edwards |
| 4,198,403 A | 4/1980 | Alvarez |
| 4,221,787 A | 9/1980 | Bodor et al. |
| 4,261,984 A | 4/1981 | Alvarez |
| 4,263,289 A | 4/1981 | Edwards |
| 4,267,173 A | 5/1981 | Draper |
| 4,285,937 A | 8/1981 | Kalvoda |
| 4,310,466 A | 1/1982 | Edwards |
| 4,335,121 A | 6/1982 | Phillips et al. |
| 4,377,575 A | 3/1983 | Phillips et al. |
| 4,472,393 A | 9/1984 | Shapiro |
| 4,607,028 A | 8/1986 | Schmidlin |
| 4,710,495 A | 12/1987 | Bodor |
| 4,861,765 A | 8/1989 | Jouveinal |
| 4,992,474 A | 2/1991 | Skidmore et al. |
| 4,994,439 A | 2/1991 | Longnecker et al. |
| 4,996,335 A | 2/1991 | Bodor |
| 5,081,113 A | 1/1992 | Claussner et al. |
| 5,202,316 A | 4/1993 | Claussner et al. |
| 5,250,293 A | 10/1993 | Gleich |
| 5,362,721 A | 11/1994 | Stache et al. |
| 5,420,120 A | 5/1995 | Boltralik |
| 5,658,549 A | 8/1997 | Akehurst et al. |
| 5,707,984 A | 1/1998 | Tjoeng et al. |
| 5,837,699 A | 11/1998 | Sequeira et al. |
| 5,849,265 A | 12/1998 | Li-Bovet et al. |
| 5,889,015 A | 3/1999 | Sequeira et al. |
| 5,919,776 A | 7/1999 | Hagmann et al. |
| 5,972,920 A | 10/1999 | Seidel |
| 5,981,517 A | 11/1999 | Bodor |
| 6,057,307 A | 5/2000 | Sequeira et al. |
| 6,127,353 A | 10/2000 | Yuen et al. |
| 6,136,294 A | 10/2000 | Adjei et al. |
| 6,197,761 B1 | 3/2001 | Biggadike et al. |
| 6,261,539 B1 | 7/2001 | Adjei et al. |
| 6,395,300 B1 | 5/2002 | Straub et al. |
| 6,537,983 B1 | 3/2003 | Biggadike et al. |
| 2002/0081266 A1 | 6/2002 | Woolfe et al. |
| 2002/0103392 A1 | 8/2002 | Stache et al. |
| 2002/0165211 A1 | 11/2002 | Biggadike et al. |
| 2002/0173496 A1 | 11/2002 | Bigggadike |

(Continued)

FOREIGN PATENT DOCUMENTS

BE 889563 11/1981

(Continued)

OTHER PUBLICATIONS

Janette M. Mahoney et al., "Drug effects on the neovascularization response to silver nitrate cauterization of the rat cornea" Current Eye Research, vol. 4, No. 5, 1985, pp. 531-535.

(Continued)

*Primary Examiner*—Barbara P. Badio
(74) *Attorney, Agent, or Firm*—James P. Riek

(57) ABSTRACT

The present invention relates to, for example, a compound of formula (X)

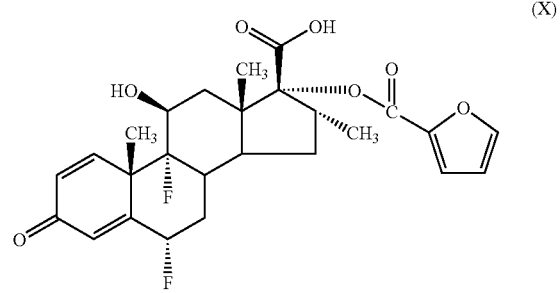

useful in the manufacture of anti-inflammatory androstane derivatives.

1 Claim, 5 Drawing Sheets

U.S. PATENT DOCUMENTS

| | | | |
|---|---|---|---|
| 2002/0177581 | A1 | 11/2002 | Biggadike |
| 2003/0073676 | A1 | 4/2003 | Biggadike et al. |
| 2003/0109511 | A1 | 6/2003 | Biggadike et al |
| 2003/0144257 | A1 | 7/2003 | Biggadike et al. |
| 2003/0158163 | A1 | 8/2003 | Cuenoud et al. |

FOREIGN PATENT DOCUMENTS

| | | |
|---|---|---|
| DE | 1059906 | 6/1959 |
| DE | 2031205 | 2/1971 |
| DE | 2336693 | 2/1975 |
| DE | 2538569 | 3/1977 |
| EP | 0004773 | 10/1979 |
| EP | 0057401 | 8/1982 |
| EP | 0135476 | 3/1985 |
| EP | 0179583 | 4/1986 |
| EP | 0389369 | 9/1990 |
| EP | 0416951 | 3/1991 |
| EP | 0418716 | 3/1991 |
| EP | 0470617 | 2/1992 |
| EP | 0521455 | 1/1993 |
| EP | 0640616 | 3/1995 |
| EP | 0646593 | 4/1995 |
| FR | 580494 | 10/1986 |
| GB | 1296458 | 11/1972 |
| GB | 1384372 | 2/1975 |
| GB | 1438940 | 6/1976 |
| GB | 1517278 | 7/1978 |
| GB | 2079755 | 1/1982 |
| GB | 2140800 | 12/1984 |
| IL | 109656 | 2/1998 |
| JP | 04208267 | 7/1992 |
| JP | 8291072 | 11/1996 |
| JP | 8291073 | 11/1996 |
| WO | WO 89/03390 | 4/1989 |
| WO | 0389368 | 9/1990 |
| WO | 92/14472 | 9/1992 |
| WO | 94/21229 | 9/1994 |
| WO | 95/31964 | 11/1995 |
| WO | 96/19199 | 6/1996 |
| WO | 97/05136 | 2/1997 |
| WO | 97/15298 | 5/1997 |
| WO | 97/24365 | 7/1997 |
| WO | WO 97/21721 | 9/1997 |
| WO | WO 97/21724 | 9/1997 |
| WO | WO 97/40836 | 11/1997 |
| WO | 97/46243 | 12/1997 |
| WO | 98/17676 | 4/1998 |
| WO | 98/34596 | 8/1998 |
| WO | 98/43630 | 10/1998 |
| WO | 99/01467 | 1/1999 |
| WO | 99/25359 | 5/1999 |
| WO | 99/32089 | 7/1999 |
| WO | 00/16814 | 3/2000 |
| WO | 00/33892 | 6/2000 |
| WO | 00/38811 | 7/2000 |
| WO | 00/57401 | 8/2000 |
| WO | WO 00/49993 | 8/2000 |
| WO | WO 00/66522 | 11/2000 |
| WO | 01/04118 | 1/2001 |
| WO | 01/15744 | 3/2001 |
| WO | 01/20331 | 3/2001 |
| WO | 01/54664 | 8/2001 |
| WO | 01/62722 | 8/2001 |
| WO | 01/78736 | 10/2001 |
| WO | 01/78739 | 10/2001 |
| WO | 01/78741 | 10/2001 |
| WO | 01/78745 | 10/2001 |
| WO | 02/00199 | 1/2002 |
| WO | 02/00679 | 1/2002 |
| WO | 02/007767 | 1/2002 |
| WO | 02/008243 | 1/2002 |
| WO | 02/012265 | 2/2002 |
| WO | 02/012266 | 2/2002 |
| WO | 02/013668 | 2/2002 |
| WO | 02/26723 | 4/2002 |
| WO | 02/053186 | 7/2002 |
| WO | 02/066422 | 8/2002 |
| WO | 02/070490 | 9/2002 |
| WO | 02/076933 | 10/2002 |
| WO | 02/085296 | 10/2002 |
| WO | 02/088167 | 11/2002 |
| WO | 02/100879 | 12/2002 |
| WO | 03/013427 | 2/2003 |
| WO | 03/033000 | 4/2003 |
| WO | 03/035668 | 5/2003 |
| WO | 03/040691 | 5/2003 |
| WO | 03/042229 | 5/2003 |
| WO | 03/042230 | 5/2003 |
| WO | WO 03/066656 | 8/2003 |
| ZA | 872389 | 4/1987 |

OTHER PUBLICATIONS

Richard A. Kenley et al., "An Automated, Column-Switching HPLC Method for Analyzing Active and Excipient Materials in Both Cream and Ointment Formulations," Drug Development and Industrial Pharmacy, vol. 11 (9&10), 1985, pp. 1781-1796.

R. Woodford et al., "Activity and bioavailability of a new steroid (Timobesone acetate) in cream and ointment compared with Lidex and Dermovate creams and ointments and Betnovate cream" Int'l Journal of Pharmaceutics, vol. 26 (1985) pp. 145-155.

Denis J. Kertesz et al., "Thiol Esters from Steroid 17β-Carboxylic Acids: Carboxylate Activation and Internal Participation by 17 α-Acylates" J. Org. Chem., vol. 51, 1986, pp. 2315-2328.

Popper, T.L., et al., "Structure-Activity Relationship of a series of novel topical corticosteroids", Journal of Steroid Biochemistry 1987, vol. 27, 840-841.

Shapiro, E.L., et al. Al., "17 Heteroaroyl Esters of Corticosteriods 2. 11 Beta Hydroxy Series." Journal of Medicinal Chemistry, American Chemical Society, Washington, US, vol. 30, No. 9, 1987, pp. 1581-1588.

John T. H. Ong et al., "Micellar Solubilization of Timobesone Acetate in Aqueous and Aqueous Propylene Glycol Solutions of Nonionic Surfactants", Pharmaceutical Research, vol. 5, No. 11, 1988, pp. 704-708.

John T. H. Ong et al., Intrinsic Potencies of Novel Thiol Ester Corticosteroids RS-85095 and RS-21314 as Compared With Clobetasol 17-Propionate and Fluocinonide Arch Dermatol, vol. 125, Dec. 1989, pp. 1662-1665.

Isogai, Mitsutaka, et al., "Binding affinities of Mometasone Furoate and related compounds including its Metabolites for the Glucocorticoid Receptor of Rat Skin Tissue" J. Steroid Biochem. Mol. Biol. 1993, vol. 44, 141-145.

Phillips, GH et al., "Synthesis and structure activity Relationships in a series of Anti-inflammatory Corticosteroid Analogues, Halomethyl Androstane—17B-carbothioates and—17B-carboselenoates," Journal of Medicinal Chemistry 1994, 37, 3717-3729.

S.J. Lane et al., "Evaluation of a New Capillary Electrochromatography/Mass Spectrometry Interface Using Short Columns and High Field Strengths for Rapid and Efficient Analyses," Rapid Communications in Mass Spectrometry, vol. 10, 1996, pp. 733-736.

Franklin I. Aigbirhio et al., "Automated Radiosynthesis of No-carrier-added [S-fluoromethyl-$^{18}$F]Fluticasone Propionate as a Radiotracer for Lung Deposition Studies with PET" Journal of Labelled Compounds and Radiopharmaceuticals, vol. 39, No. 7, 1997, pp. 569-584.

Nisha Mistry et al., "Characterisation of impurities in bulk drug batches of fluticasone propionate using directly coupled HPLC-NMR spectroscopy and HPLC-MS," Journal of Pharmaceutical and Biomedical Analysis vol. 16, 1997, pp. 697-705.

Knobil, K., et al. Al., "Adding Salmeterol Is More Effective Than Increasing The Dose Of Fluticasone For Patients With Asthma Who Are Symptomatic On Low Dose Fluticasone," European Respiratory review, Copenhagen, DK, vol. 12, no. SUPPL Dec. 29, 1998, pp. 19S-20S.

Nisha Mistry et al., Impurity profiling in bulk pharmaceutical batches using 19F NMR spectroscopy and distinction between monomeric and dimeric impurities by NMR-based diffusion measurements, Journal of Pharmaceutical and Biomedical Analysis, vol. 19, 1999, pp. 511-517.

N. Smith et al., "Comparison of the electroosmotic flow profiles and selectivity of stationary Phases used in capillary electrochromatography," Journal of Chromatography A., vol. 832, 1999, pp. 44-54.

R.C. Garner et al., "A validation study comparing accelerator MS and liquid scintillation counting for analysis of $^{14}$C-labelled drugs in plasma, urine and faecal extracts", Journal of Pharmaceutical and Biomedical Analysis vol. 24, 2000, pp. 197-209.

Harold S. Nelson et al. "Fluticasone propionate/salmeterol combination provides more effective asthma control than low-dose inhaled corticosteroid plus montelukast," J. Allergy Clin. Immunol., vol. 106, No. 6, Dec. 2000, pp. 1088-1095.

Gunnar Johansson et al., "Comparison of Salmeterol/Fluticasone Propionate Combination With Budesonide in Patients With Mild-to-Moderate Asthma" Clin. Drug Invest. vol. 21, No. 9, 2001, pp. 633-642.

Bertil Pettersson et al., Re-evaluation of the classical *Mycoplasma lipophilum* cluster (Weisburg et al. 1989) and description of two new clusters in the hominis group based on 16S rDNA sequences, Int'l Journal of Systematic & Evolutionary Microbiology (2001) vol. 51, pp. 633-643.

Sarah A. Lewis et al., "Association of specific allergen sensitization with socioeconomic factors and allergic disease in a population of Boston women", J. Allergy Clin. Immunol., vol. 107, No. 4, Apr. 2001, pp. 615-622.

Katherine A. Lyseng-Williamson et al., "Inhaled Salmeterol/ Fluticasone Propionate Combination in Chronic Obstructive Pulmonary Disease," Am. J. Respir. Med. vol. 1, No. 4, 2002, pp. 273-282.

Jeffrey W. Millard et al., "Solubilization by cosolvents Establishing useful constants for the log-linear model," Int'l Journal of Pharmaceutics vol. 245, 2002, pp. 153-166.

C. Baumgarten et al., "Initial Treatment of Symptomatic Mild to Moderate Bronchial Asthma with the Salmeterol/Fluticasone Propionate (50/250μg) Combination Product (SAS 40023)" European Journal of Medical Research 2002, vol. 7, pp. 1-7.

Stephen J. Fowler et al., "Step-down therapy with low-dose fluticasone-salmeterol combination or medium-dose hydrofluoroalkane 134a-beclomethasone alone" J. Allergy Clin. Immunol., vol. 109, No. 6, Jun. 2002, pp. 929-935.

Elizabeth F. Juniper et al., "Impact of Inhaled Salmeterol/ Fluticasone Propionate Combination Product versus Budesonide on the Health-Related Quality of Life of Patients with Asthma," Am. J. Respir. Med., vol. 1, No. 6, 2002, pp. 435-440.

William Busse et al., "Steroid-sparing effects of fluticasone propionate 100 μg and salmeterol 50 μg administered twice daily in a single product in patients previously controlled with fluticaasone propionate 250 μg administered twice daily" J. Allergy Clin. Immunol., vol. 111, No. 1, Jan. 2003, pp. 57-65.

Ueno H et al, "Synthesis and Evaluation of Antiinflammatory Activities of a series of Corticosteroid 17. Alpha -Esters Containing a Functional Group",Journal of Medicinal Chemistry, American Chemical Society, vol. 34, No. 8, Aug. 1991, pp. 2468-2473.

Peter J Barnes, "Novel approaches and targets for treatment of Chronic Obstructive Pulmonary Disease" American Journal of Respiratory and Critical Care Medicine, vol. 160, 1999, pp. S72-S79.

B.J O Conner: "Combination Therapy", Pulmonary Pharmacology and Therapeutics, vol. 11, No. 5/6, 1998, pp. 397-399.

Peter J Barnes, "Chronic Obstructive Pulmonary Disease: new opportunities for drug development" Trends in Pharmacological Sciences, Elsevenir Trends Journal, vol. 19, No. 10, 1998, pp. 415-423.

Simon Bowler,"Long acting beta agonists", Austrailian Family Physician, vol. 27, No. 12, 1998, pp. 1114-1118.

Naedle-Risha R et al, "Dual components of optimal asthma therapy: scientific and clinical rationale for the use of long acting beta-agonists with inhaled corticosteroids", The Journal of the American Osteopathic Association, vol. 101, No. 9, Sep. 2001, pp. 2001-2009.

T Van Der Molen et al, "Effects of the Long Acting Beta Agonist Formoterol on Asthma Control in Asthmatic Patients Using Inhaled Corticosteroids", vol. 52, No. 6, 1997, pp. 535-539.

B.N. Lutsky et al, "A Novel Class of potent Topical Anti-inflammatory Agents: 17 Benzoylated, 7—Halogeno substituted Corticosteroids", Arzeneimittel Forschung, vol. 29, No. 11, Nov. 1979, pp. 1662-1667.

Peter J. Barnes, "Efficacy of Inhaled Corticosteroids in Asthma", The Journal of Allergy and Clinical Immunology, vol. 102, No. 4, pp. 531-538, 1998.

CAS Registry No. 102113-40-6.

Li et al., "Synthesis of aryl 5-(2-chlorophenyl)-2-furoates under phase transfer catalysis," *Synthetic Communications* 32(20):3081-3086 (2002).

Moreno-Vargas et al., "Synthesis and glycosidase inhibitory activities of 5-(1',4'-dideoxy-1',4'-imino-D-erythrosyl)-2-methyl-3-furoic acid (=5-[(3S,4R)-3,4-dihydroxypyrrolidin-2-yl]-2methylfuran-3-carboxylic acid) derivatives: New leads as selective α-L-fucosidase and β-galactosidase inhibitors," *Helvetica Chimica Acta* 86:1894-1913 (2003).

Tanaka et al., "Synthesis of 4H-furo[3,2-b]indole derivatives. III (1). Preparation of 4H-furo[3,2-b]indole-2-carboxylic acid derivatives," *Journal Heterocyclic Chemistry* 16:785-788 (1979).

Wenkert et al., "Short syntheses of furan and catechol derivatives. A synthesis of hydrourushiol[1,2]," *Journal American Chemical Society* 105:2021-2029 (1983).

U.S. Appl. No. 10/066,964, filed Feb. 4, 2002.
U.S. Appl. No. 10/067,010, filed Feb. 4, 2002.
U.S. Appl. No. 10/066,836, filed Feb. 4, 2002.
U.S. Appl. No. 10/200,364, filed Jul. 22, 2002.
U.S. Appl. No. 10/281,735, filed Oct. 28, 2002.
U.S. Appl. No. 10/241,658, filed Sep. 11, 2002.
U.S. Appl. No. 10/066,951, filed Feb. 4, 2002.
U.S. Appl. No. 10/067,020, filed Feb. 4, 2002.

Sakagami et al., "Mucoadhexive BDP microspheres for powder inhalation-their unique pharmacokinetic-pharmacodynamic profiles," *Respiratory Drug Delivery VI*, pp. 193-199 (1998.).

PCT/GB01/03495 Written Opinion, date of mailing Apr. 4, 2002.

PCT/GB01/03495 International Preliminary Examination report, date of mailing Aug. 30, 2002.

Pharmacokinetics of GW685698X and CC118781 (Fluticasone Propionate) when Co-Administered by the Intratracheal or Intravenous Route to the Anaesthetised White Pig (Study No. 03DMW062) 2004.

The Pharmacokinetics of GW685698X and CC118781 Following Intratracheal Co-Administration to the Anaesthetised White Pig (Study No. B30947) 2003.

COMPOUNDS USEFUL IN THE MANUFACTURE OF AN ANTI-INFLAMMATORY ANDROSTANE DERIVATIVE

CROSS-REFERENCE TO RELATED APPLICATIONS

The present application is a Divisional Application of U.S. Ser. No. 09/958,050, filed 2 Oct. 2001, which was a national stage filing of PCT/GB01/03495 filed 3 Aug. 2001 filed under 35 USC 371, and which claimed priority from British Patent Application GB0019172.6 filed 5 Aug. 2000.

FIELD OF THE INVENTION

The present invention relates to a novel compounds, such compounds having utility in in the manufacture of novel anti-inflammatory and anti-allergic compounds of the androstane series.

BACKGROUND OF THE INVENTION

Glucocorticoids which have anti-inflammatory properties are known and are widely used for the treatment of inflammatory disorders or diseases such as asthma and rhinitis. For example, U.S. Pat. No. 4,335,121 discloses 6α, 9α-Difluoro-17α-(1-oxopropoxy)-11β-hydroxy-16α-methyl-3-oxo-androsta-1,4-diene-17β-carbothioic acid S-fluoromethyl ester (known by the generic name of fluticasone propionate) and derivatives thereof. The use of glucocorticoids generally, and especially in children, has been limited in some quarters by concerns over potential side effects. The side effects that are feared with glucocorticoids include suppression of the Hypothalamic-Pituitary-Adrenal (HPA) axis, effects on bone growth in children and on bone density in the elderly, ocular complications (cataract formation and glaucoma) and skin atrophy. Certain glucocorticoid compounds also have complex paths of metabolism wherein the production of active metabolites may make the pharmacodynamics and pharmacokinetics of such compounds difficult to understand. Whilst the modern steroids are very much safer than those originally introduced, it remains an object of research to produce new molecules which have excellent anti-inflammatory properties, with predictable pharmacokinetic and pharmacodynamic properties, with an attractive side effect profile, and with a convenient treatment regime.

BRIEF SUMMARY OF THE INVENTION

We have now identified a novel glucocorticoid compound which substantially meets these objectives.

Thus, according to one aspect of the invention, there is provided a compound of formula (I)

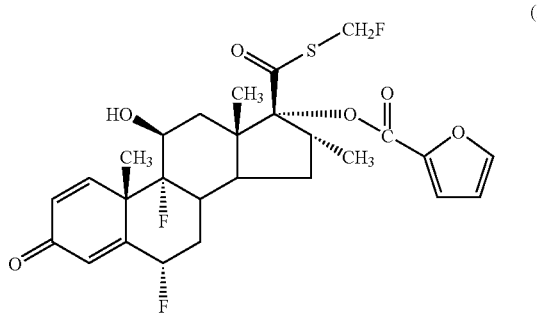

and solvates thereof.

The chemical name of the compound of formula (I) is 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester.

References hereinafter to the compound according to the invention include both the compound of formula (I) and solvates thereof, particularly pharmaceutically acceptable solvates.

The compound of formula (I) has potentially beneficial anti-inflammatory or anti-allergic effects, particularly upon topical administration, demonstrated by, for example, its ability to bind to the glucocorticoid receptor and to illicit a response via that receptor. Hence, the compound of formula (I) is useful in the treatment of inflammatory and/or allergic disorders.

Compound (I) undergoes highly efficient hepatic metabolism to yield the 17-β carboxylic acid (X) as the sole major metabolite in rat and human in vitro systems. This metabolite has been synthesised and demonstrated to be >1000 fold less active than the parent compound in in vitro functional glucocorticoid assays.

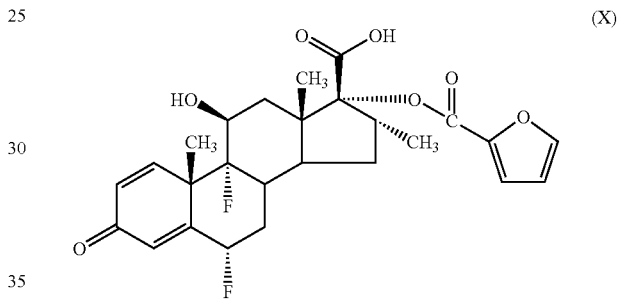

This efficient hepatic metabolism is reflected by in vivo data in the rat, which have demonstrated plasma clearance at a rate approaching hepatic blood flow and an oral bioavailability of <1%, consistent with extensive first-pass metabolism.

In vitro metabolism studies in human hepatocytes have demonstrated that compound (I) is metabolised in an identical manner to fluticasone propionate but that conversion of (I) to the inactive acid metabolite occurs approximately 5-fold more rapidly than with fluticasone propionate. This very efficient hepatic inactivation would be expected to minimise systemic exposure in man leading to an improved safety profile.

Inhaled steroids are also absorbed through the lung and this route of absorption makes a significant contribution to systemic exposure. Reduced lung absorption could therefore provide an improved safety profile. Studies with compound of formula (I) have shown significantly lower exposure to compound of formula (I) than with fluticasone propionate after dry powder delivery to the lungs of anaesthetised pigs.

An improved safety profile is believed to allow the compound of formula (I) to demonstrate the desired anti-inflammatory effects when administered once-per day. Once-per-day dosing is considered to be significantly more convenient to patients than the twice-per day dosing regime that is normally employed for fluticasone propionate.

Examples of disease states in which the compound of the invention has utility include skin diseases such as eczema, psoriasis, allergic dermatitis, neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

The compound of the invention may also have use in the treatment of conjunctiva and conjunctivitis.

It will be appreciated by those skilled in the art that reference herein to treatment extends to prophylaxis as well as the treatment of established conditions.

As mentioned above, the compound of formula (I) is useful in human or veterinary medicine, in particular as an anti-inflammatory and anti-allergic agent.

There is thus provided as a further aspect of the invention the compound of formula (I) or a physiologically acceptable solvate thereof for use in human or veterinary medicine, particularly in the treatment of patients with inflammatory and/or allergic conditions, especially for treatment once-per-day.

According to another aspect of the invention, there is provided the use of the compound of formula (I) or physiologically acceptable solvate thereof for the manufacture of a medicament for the treatment of patients with inflammatory and/or allergic conditions, especially for treatment once-per-day.

In a further or alternative aspect, there is provided a method for the treatment of a human or animal subject with an inflammatory and/or allergic condition, which method comprises administering to said human or animal subject an effective amount of the compound of formula (I) or physiologically acceptable solvate thereof, especially for administration once-per-day.

The compound according to the invention may be formulated for administration in any convenient way, and the invention therefore also includes within its scope pharmaceutical compositions comprising the compound of formula (I) or a physiologically acceptable solvate thereof together, if desirable, in admixture with one or more physiologically acceptable diluents or carriers. Pharmaceutical compositions suitable for once-per-day administration are of particular interest.

Further, there is provided a process for the preparation of such pharmaceutical compositions which comprises mixing the ingredients.

The compound according to the invention may, for example, be formulated for oral, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (eg eye or nose drops), solutions/suspensions for nebulisation, suppositories, pessaries, retention enemas and chewable or suckable tablets or pellets (eg for the treatment of aphthous ulcers) or liposome or microencapsulation preparations.

Advantageously compositions for topical administration to the lung include dry powder compositions and spray compositions.

Dry powder compositions for topical delivery to the lung may, for example, be presented in capsules and cartridges for use in an inhaler or insufflator of, for example, gelatine. Formulations generally contain a powder mix for inhalation of the compound of the invention and a suitable powder base such as lactose or starch. Each capsule or cartridge may generally contain between 20 µg–10 mg of the compound of formula (I). Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Pharmaceutical formulations which are non-pressurised and adapted to be administered as a dry powder topically to the lung via the buccal cavity (especially those which are free of excipient or are formulated with a diluent or carrier such as lactose or starch, most especially lactose) are of particular interest.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants eg oleic acid or lecithin and cosolvents eg ethanol. One example formulation is excipient free and consists essentially of (eg consists of) compound of formula (I) (preferably in unsolvated form eg as Form 1) (optionally in combination with another therapeutically active ingredient) and a propellant selected from 1,1,1,2-tetrafluoroethane, 1,1,1,2,3,3,3-heptafluoro-n-propane and mixture thereof. Another example formulation comprises particulate compound of formula (I), a propellant selected from 1,1,1,2-tetrafluoroethane, 1,1,1,2,3,3,3-heptafluoro-n-propane and mixture thereof and a suspending agent which is soluble in the propellant eg an oligolactic acid or derivative thereof as described in WO94/21229. The preferred propellant is 1,1,1,2-tetrafluoroethane. As noted elsewhere in this specification, compound of formula (I) does not appear to form a solvate with 1,1,1,2-tetrafluoroethane. Pressurised formulations will generally be retained in a canister (eg an aluminium canister) closed with a valve (eg a metering valve) and fitted into an actuator provided with a mouthpiece.

Pressurised aerosol formulations preferably do not comprise particulate medicament, a propellant and a stabiliser comprising a water addition (i.e. water added in addition to nascent formulation water). Pressurised aerosol formulations also preferably do not comprise particulate medicament, a propellant and a stabiliser comprising an amino acid, a derivative thereof or a mixture thereof.

Medicaments for administration by inhalation desirably have a controlled particle size. The optimum particle size for inhalation into the bronchial system is usually 1–10 μm, preferably 2–5 μm. Particles having a size above 20 μm are generally too large when inhaled to reach the small airways. To achieve these particle sizes the particles of compound of formula (I) as produced may be size reduced by conventional means eg by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I) as medicament in a liquid solvent with a flowing liquid antisolvent for said medicament (eg as described in International Patent Application PCT/GB99/04368) or else by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (eg as described in International Patent Application PCT/GB00/04327). When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60–90 μm and not less than 15% will have a MMD of less than 15 μm.

Formulations for administration topically to the nose (eg for the treatment of rhinitis) include pressurised aerosol formulations and aqueous formulations administered to the nose by pressurised pump. Formulations which are non-pressurised and adapted to be administered topically to the nasal cavity are of particular interest. The formulation preferably contains water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

Other possible presentations include the following:

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

If appropriate, the formulations of the invention may be buffered by the addition of suitable buffering agents.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will usually be within the range of from 0.1 to 5%.

Aerosol formulations are preferably arranged so that each metered dose or "puff" of aerosol contains 1 μg–2000 μg eg 20 μg–2000 μg, preferably about 20 μg–500 μg of a compound of formula (I). Administration may be once daily or several times daily, for example 2, 3, 4 or 8 times, giving for example 1, 2 or 3 doses each time. Preferably the compound of formula (I) is delivered once or twice daily, more preferably once per day. The overall daily dose with an aerosol will typically be within the range 10 μg–10 mg eg 100 μg–10 mg preferably, 200 μg–2000 μg.

Topical preparations may be administered by one or more applications per day to the affected area; over skin areas occlusive dressings may advantageously be used. Continuous or prolonged delivery may be achieved by an adhesive reservoir system.

For internal administration the compound according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the compound of the invention.

The compound according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, eg 5–30 mg, dependent on the condition being treated, and the duration of treatment desired.

Slow release or enteric coated formulations may be advantageous, particularly for the treatment of inflammatory bowel disorders.

The pharmaceutical compositions according to the invention may also be used in combination with another therapeutically active agent, for example, a $\beta_2$ adrenoreceptor agonist, an anti-histamine or an anti-allergic. The invention thus provides, in a further aspect, a combination comprising the compound of formula (I) or a physiologically acceptable solvate thereof together with another therapeutically active agent, for example, a $\beta_2$-adrenoreceptor agonist, an anti-histamine or an anti-allergic.

Examples of $\beta_2$-adrenoreceptor agonists include salmeterol (eg as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Examples of anti-histamines include methapyrilene or loratadine.

Other suitable combinations include, for example, other anti-inflammatory agents eg NSAIDs (eg sodium cromoglycate, nedocromil sodium, PDE4 inhibitors, leukotriene antagonists, iNOS inhibitors, tryptase and elastase inhibitors, beta-2 integrin antagonists and adenosine 2a agonists)) or antiinfective agents (eg antibiotics, antivirals).

Of particular interest is use of the compound of formula (I) in combination with a phosphodiesterase 4 (PDE4) inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

Initial experiments were conducted to establish and validate a [$^3$H]-rolipram binding assay. Details of this work are given in the Binding Assays described in detail below.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Examples of useful PDE4 inhibitors are:
(R)-(+)-1-(4-bromobenzyl)-4-[(3-cyclopentyloxy)-4-methoxyphenyl]-2-pyrrolidone;
(R)-(+)-1-(4-bromobenzyl)-4-[(3-cyclopentyloxy)-4-methoxyphenyl]-2-pyrrolidone;
3-(cyclopentyloxy-4-methoxyphenyl)-1-(4-N'-[N2-cyano-S-methyl-isothioureido]benzyl)-2-pyrrolidone;
cis 4-cyano-4-[(3-cyclopentyloxy-4-methoxyphenyl)cyclohexan-1-carboxylic acid];
cis-[4-cyano-4-(3-cyclopropylmethoxy-4-difluoromethoxyphenyl)cyclohexan-1-ol];
(R)-(+)-ethyl [4-(3-cyclopentyloxy-4-methoxyphenyl)pyrrolidine-2-ylidene]acetate; and
(S)-(−)-ethyl [4-(3-cyclopentyloxy-4-methoxyphenyl)pyrrolidine-2-ylidene]acetate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]; these are examples of compounds which bind preferentially to the low affinity binding site and which have an $IC_{50}$ ratio of 0.1 or greater.

Other compounds of interest include:
Compounds set out in U.S. Pat. No. 5,552,438 issued 3 Sep., 1996; this patent and the compounds it discloses are incorporated herein in full by reference. The compound of particular interest, which is disclosed in U.S. Pat. No. 5,552,438, is cis-4-cyano-4-[3-(cyclopentyloxly)-4-methoxyphenyl]cyclohexane-1-carboxylic acid (also known as cilomalast) and its salts, esters, pro-drugs or physical forms;

AWD-12-281 from Astra (Hofgen, N. et al. 15th EFMC Int Symp Med Chem (September 6–10, Edinburgh) 1998, Abst P.98); a 9-benzyladenine derivative nominated NCS-613 (INSERM); D-4418 from Chiroscience and Schering-Plough; a benzodiazepine PDE4 inhibitor identified as CI-1018 (PD-168787; Parke-Davis/Warner-Lambert); a benzodioxole derivative Kyowa Hakko disclosed in WO 9916766; V-11294A from Napp (Landells, L. J. et al. Eur Resp J [Annu Cong Eur Resp Soc (September 19–23, Geneva) 1998] 1998, 12(Suppl. 28): Abst P2393); roflumilast (CAS reference No 162401-32-3) and a pthalazinone (WO 9947505) from Byk-Gulden; or a compound identified as T-440 (Tanabe Seiyaku; Fuji, K. et al. J Pharmacol Exp Ther,1998, 284(1): 162).

Phosphodiesterase and Rolipram Binding Assays

Assay Method 1A

Isolated human monocyte PDE4 and hrPDE (human recombinant PDE4) was determined to exist primarily in the low affinity form. Hence, the activity of test compounds against the low affinity form of PDE4 can be assessed using standard assays for PDE4 catalytic activity employing 1 μM [$^3$H]cAMP as a substrate (Torphy et al., J. of Biol. Chem., Vol. 267, No. 3 pp1798–1804, 1992).

Rat brain high speed supernatants were used as a source of protein and both enantiomers of [$^3$H]-rolipram were prepared to a specific activity of 25.6 Ci/mmol. Standard assay conditions were modified from the published procedure to be identical to the PDE assay conditions, except for the last of the cAMP: 50mM Tris HCl (pH 7.5), 5 mM $MgCl_2$, 50 μM 5'-AMP and 1 nM of [$^3$H]-rolipram (Torphy et al., J. of Biol. Chem., Vol. 267, No. 3 pp1798–1804, 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [$^3$H]-cAMP was not present.

Assay Method 1B

Measurement of Phosphodiesterase Activity

PDE activity was assayed using a [$^3$H]cAMP SPA or [3H]cGMP SPA enzyme assay as described by the supplier (Amersham Life Sciences). The reactions were conducted in 96-well plates at room temperature, in 0.1 ml of reaction buffer containing (final concentrations): 50 mM Tris-HCl, pH 7.5, 8.3 mM $MgCl_2$, 1.7 mM EGTA, [$^3$H]cAMP or [$^3$H]

cGMP (approximately 2000 dpm/pmol), enzyme and various concentrations of the inhibitors. The assay was allowed to proceed for 1 hr and was terminated by adding 50 μl of SPA yttrium silicate beads in the presence of zinc sulfate. The plates were shaken and allowed to stand at room temperature for 20 min. Radiolabeled product formation was assessed by scintillation spectrometry.

[$^3$H]R-rolipram Binding Assay

The [$^3$H]R-rolipram binding assay was performed by modification of the method of Schneider and co-workers, see Nicholson, et al., Trends Pharmacol. Sci., Vol. 12, pp.19–27 (1991) and McHale et al., Mol. Pharmacol., Vol. 39, 109–113 (1991). R-Rolipram binds to the catalytic site of PDE4 see Torphy et al., Mol. Pharmacol., Vol. 39, pp. 376–384 (1991). Consequently, competition for [$^3$H]R-rolipram binding provides an independent confirmation of the PDE4 inhibitor potencies of unlabeled competitors. The assay was performed at 30° C. for 1 hr in 0.5 μl buffer containing (final concentrations): 50 mM Tris-HCl, pH 7.5, 5 mM MgCl$_2$, 0.05% bovine serum albumin, 2 nM [$^3$H]R-rolipram (5.7×104 dpm/pmol) and various concentrations of non-radiolabeled inhibitors. The reaction was stopped by the addition of 2.5 ml of ice-cold reaction buffer (without [$^3$H]-R-rolipram) and rapid vacuum filtration (Brandel Cell Harvester) through Whatman GF/B filters that had been soaked in 0.3% polyethylenimine. The filters were washed with an additional 7.5 ml of cold buffer, dried, and counted via liquid scintillation spectrometry.

The invention thus provides, in a further aspect, a combination comprising the compound of formula (I) or a physiologically acceptable solvate thereof together with a PDE4 inhibitor.

The combination referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

Surprisingly, the compound of formula (I) has demonstrated a significant propensity to form solvates with commonly used organic solvents. Such solvates are essentially stoichiometric eg the ratio of compound of formula (I) to solvent is close to 1:1 eg according to Applicant's analysis has been determined to be in the range 0.95–1.05: 1. For example, we have prepared solvates with solvents such as acetone, dimethylformamide (DMF), dimethylacetamide (DMAc), tetrahydrofuran (THF), N-methyl-2-pyrrolidone, isopropanol and methylethylketone. The solvation of compound of formula (I) is not predictable however since we have found that even though it does form a solvate with isopropanol it does not appear to form a solvate with ethanol or methanol. Furthermore it does not appear to form a solvate with 1,1,1,2-tetrafluoroethane, ethylacetate, methylacetate, toluene, methylisobutylketone (MIBK) or water either. However due to the toxicity of many organic solvents it has been necessary to develop special final stage processing conditions (discussed later) in order to permit the compound of formula (I) to be produced in unsolvated form. Thus according to another aspect of the invention there is provided a compound of formula (I) in unsolvated form.

Surprisingly we have also discovered that the compound of formula (I) in unsolvated form may exist in a number of polymorphic forms. Specifically we have identified polymorphic forms which may be distinguished by means of X-Ray Powder Diffraction (XRPD) which we have named as Form 1, Form 2 and Form 3. Form 3 appears to be an unstable minor polymorphic modification of Form 2. Broadly speaking the Forms are characterised in their XRPD profiles as follows:

Form 1: Peak at around 18.9 degrees 2Theta

Form 2: Peaks at around 18.4 and 21.5 degrees 2Theta.

Form 3: Peaks at around 18.6 and 19.2 degrees 2Theta.

Within the range 21–23 degrees 2Theta Form 3 shows a single peak whereas Form 2 shows a pair of peaks. A peak at 7 degrees 2Theta is present in all cases however it is present at much higher intensity in the case of Forms 2 and 3 than is the case for Form 1.

The XRPD patterns of the polymorphs are shown overlaid in FIG. 1. The conversion of Form 2 to Form 1 with time in an aqueous slurry at ambient temperature is shown in FIG. 2. In the conversion of Form 2 to Form 1 the loss of a peak characteristic of Form 2 (labelled B) at around 18.4 degrees 2Theta, a marked reduction in intensity in the peak at around 7 degrees 2Theta (labelled A) and the appearance of a peak characteristic of Form 1 (labelled C) at around 18.9 degrees 2Theta are particularly noticeable.

The temperature dependence of Form 3 is shown in FIG. 4. The temperature was varied according to the profile shown in FIG. 5. From FIG. 4 it can be seen that Form 3 converts first to Form 2 over the temperature range 30–170° C. and then converts to Form 1 over the temperature range 170–230 ° C. In the conversion of Form 3 to Form 2 the division of one peak in the range 21–23 degrees 2Theta into two peaks within the same range and the shifting leftwards of the peak at around 18.6 degrees 2Theta to around 18.4 degrees 2Theta are particularly noticeable. In the conversion of Form 2 to Form 1 similar changes to those noted in the previous paragraph may be observed.

The differential scanning calorimetry (DSC) and thermal gravimetric analysis (TGA) profiles of Form 1 are shown in FIG. 3. The profiles are characterised by a transition at around 280–300° C. (typically close to 298° C.) corresponding to an endothermic event in the DSC and chemical degradation in the TGA. The DSC profiles of Forms 2 and 3 were not materially different under the conditions of the experiments performed and thus DSC is not a suitable technique for distinguishing between the 3 Forms. In FIG. 3 the absence of activity in the TGA and DSC profiles below around 298° C. implies that the substance shows good physical and chemical stability at normal operating temperatures.

As shown in the Examples, enthalpy of dissolution of Forms 1 and 3 have been determined in certain organic solvents and accordingly an enthalpy of transition from Form 3 to Form 1 of 5.1–6.7 kJ/mol has been estimated.

Thus we prefer compound of formula (I) in unsolvated Form 1 since this form appears to be thermodynamically most stable at ambient temperature and also appears to be least susceptible to undesirable moisture sorption (see results in Examples section). Nevertheless Form 2 (or Form 3) may be preferred under other conditions.

Although use of a compound of formula (I) in solvated form is not preferred, nevertheless we have surprisingly found that certain solvate forms have particularly attractive physicochemical properties which makes them useful as intermediates in the preparation of a compound of formula (I) in unsolvated form (eg by removal of solvent as a final step). For example we have discovered that certain stoichiometric solvates can be isolated as solids in highly crystalline form. Thus we also provide as an aspect of the invention:
Compound of formula (I) as the methylethylketone solvate
Compound of formula (I) as the isopropanol solvate
Compound of formula (I) as the tetrahydrofuran solvate
Compound of formula (I) as the acetone solvate.

In particular we provide the aforementioned solvates as solids in crystalline form. A further particular advantage of these solvates is the fact that desolvation of the solvate (eg by heating) results in formation of the unsolvated form as the preferred Form 1. The aforementioned solvates have relatively low toxicity and are suitable for use in industrial scale manufacture. Compound of formula (I) as the DMF solvate which may also be isolated as a solid in crystalline form is also of interest for use in onward processing to unsolvated Form 1.

The compound of formula (I) and solvates thereof may be prepared by the methodology described hereinafter, constituting a further aspect of this invention.

A process according to the invention for preparing a compound of formula (I) or a solvate thereof comprises alkylation of a thioacid of formula (II)

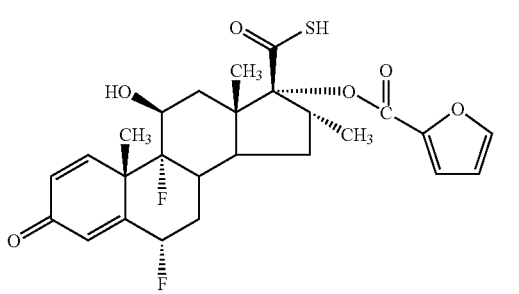

or a salt thereof.

In this process the compound of formula (II) may be reacted with a compound of formula $FCH_2L$ wherein L represents a leaving group (eg a halogen atom, a mesyl or tosyl group or the like) for example, an appropriate fluoromethyl halide under standard conditions. Preferably, the fluoromethyl halide reagent is bromofluoromethane.

As noted later, preferably the compound of formula (II) is employed as a salt, particularly the salt with diisopropylethylamine.

In a preferred process for preparing the compound of formula (I), the compound of formula (II) or a salt thereof is treated with bromofluoromethane optionally in the presence of a phase transfer catalyst. A preferred solvent is methylacetate, or more preferably ethylacetate, optionally in the presence of water. The presence of water improves solubility of both starting material and product and the use of a phase transfer catalyst results in an increased rate of reaction. Examples of phase transfer catalysts that may be employed include (but are not restricted to) tetrabutylammonium bromide, tetrabutylammonium chloride, benzyltributylammonium bromide, benzyltributylammonium chloride, benzyltriethylammonium bromide, methyltributylammonium chloride and methyltrioctylammonium chloride. THF has also successfully been employed as solvent for the reaction wherein the presence of a phase transfer catalyst again provides a significantly faster reaction rate. Preferably the product present in an organic phase is washed firstly with aqueous acid eg dilute HCl in order to remove amine compounds such as triethylamine and diisopropylethylamine and then with aqueous base eg sodium bicarbonate in order to remove any unreacted precursor compound of formula (II). As noted later, if the compound of formula (I) so produced in solution in ethylacetate is distilled and toluene added, then unsolvated Form 1 crystallises out.

Compounds of formula (II) may be prepared from the corresponding 17α-hydroxyl derivative of formula (III):

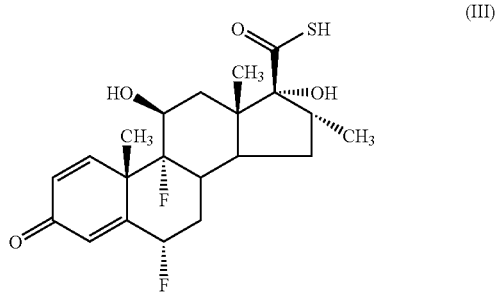

using for example, the methodology described by G. H. Phillipps et al., (1994) Journal of Medicinal Chemistry, 37, 3717–3729. For example the step typically comprises the addition of a reagent suitable for performing the esterification eg an activated derivative of 2-furoic acid such as an activated ester or preferably a 2-furoyl halide eg 2-furoyl chloride (employed in at least 2 times molar quantity relative to the compound of formula (III)) in the presence of an organic base eg triethylamine. The second mole of 2-furoyl chloride reacts with the thioacid moiety in the compound of formula (III) and needs to be removed eg by reaction with an amine such as diethylamine.

This method suffers disadvantages, however, in that the resultant compound of formula (II) is not readily purified of contamination with the by-product 2-furoyldiethylamide. We have therefore invented several improved processes for performing this conversion.

In a first such improved process we have discovered that by using a more polar amine such as diethanolamine, a more water soluble by-product is obtained (in this case 2-furoyldiethanolamide) which permits compound of formula (II) or a salt thereof to be produced in high purity since the by-product can efficiently be removed by water washing.

Thus according to this aspect of the invention we provide a process for preparing a compound of formula (II) which comprises:

(a) reacting a compound of formula (III) with an activated derivative of 2-furoic acid as in an amount of at least 2 moles of the activated derivative per mole of compound of formula (III) to yield a compound of formula (IIA)

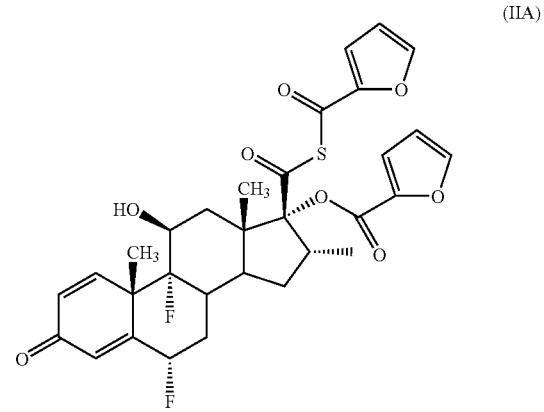

; and (b) removal of the sulphur-linked 2-furoyl moiety from compound of formula (IIA) by reaction of the product of step (a) with an organic primary or secondary amine base capable of forming a water soluble 2-furoyl amide.

In two particularly convenient embodiments of this process we also provide methods for the efficient purification of the end product which comprise either (c1) when the product of step (b) is dissolved in a substantially water immiscible organic solvent, purifying the compound of formula (II) by washing out the amide by-product from step (b) with an aqueous wash, or (c2) when the product of step (b) is dissolved in a water miscible solvent, purifying the compound of formula (II) by treating the product of step (b) with an aqueous medium so as to precipitate out pure compound of formula (II) or a salt thereof.

In step (a) preferably the activated derivative of 2-furoic acid may be an activated ester of 2-furoic acid, but is more preferably a 2-furoyl halide, especially 2-furoyl chloride. A suitable solvent for this reaction is ethylacetate or methylacetate (preferably methylacetate) (when step (c1) may be followed) or acetone (when step (c2) may be followed). Normally an organic base eg triethylamine will be present. In step (b) preferably the organic base is diethanolamine. The base may suitably be dissolved in a solvent eg methanol. Generally steps (a) and (b) will be performed at reduced temperature eg between 0 and 5° C. In step (c1) the aqueous wash may be water, however the use of brine results in higher yields and is therefore preferred. In step (c) the aqueous medium is for example a dilute aqueous acid such as dilute HCl.

According to a related aspect of the invention we provide an alternative process for preparing a compound of formula (II) which comprises:

(a) reacting a compound of formula (III) with an activated derivative of 2-furoic acid in an amount of at least 2 moles of activated derivative per mole of compound of formula (III) to yield a compound of formula (IIA); and (b) removal of the sulphur-linked 2-furoyl moiety from compound of formula (IIA) by reaction of the product of step (a) with a further mole of compound of formula (III) to give two moles of compound of formula (II).

In step (a) preferably the activated derivative of 2-furoic acid may be an activated ester of 2-furoic acid, but is more preferably a 2-furoyl halide, especially 2-furoyl chloride. A suitable solvent for his step is acetone. Normally an organic base eg triethylamine will be present. In step (b) a suitable solvent is DMF or dimethylacetamide. Normally an organic base eg triethylamine will be present. Generally steps (a) and (b) will be performed at reduced temperature eg between 0 and 5° C. The product may be isolated by treatment with acid and washing with water.

This aforementioned process is very efficient in that it does not produce any furoylamide by-product (thus affording inter alia environmental advantages) since the excess mole of furoyl moiety is taken up by reaction with a further mole of compound of formula (II) to form an additional mole of compound of formula (II).

Further general conditions for the conversion of compound of formula (III) to compound of formula (II) in the two processes just described will be well known to persons skilled in the art.

According to a preferred set of conditions, however, we have found that the compound of formula (II) may advantageously be isolated in the form of a solid crystalline salt. The preferred salt is a salt formed with a base such as triethylamine, 2,4,6-trimethylpyridine, diisopropylethylamine or N-ethylpiperidine. Such salt forms of compound of formula (II) are more stable, more readily filtered and dried and can be isolated in higher purity than the free thioacid. The most preferred salt is the salt formed with diisopropylethylamine. The triethylamine salt is also of interest.

Compounds of formula (III) may be prepared in accordance with procedures described in GB 2088877B.

Compounds of formula (III) may also be prepared by a process comprising the following steps:

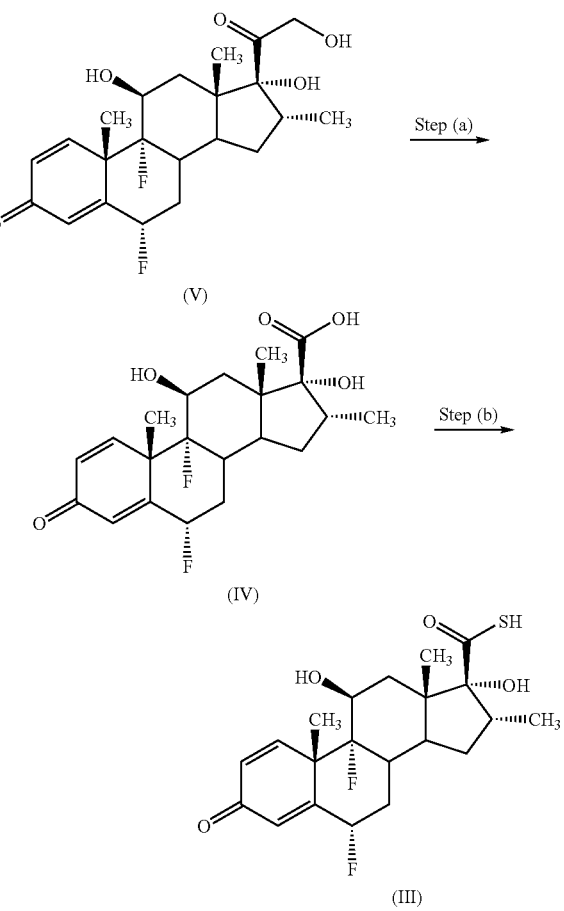

Step (a) comprises oxidation of a solution containing the compound of formula (V). Preferably, step (a) will be performed in the presence of a solvent comprising methanol, water, tetrahydrofuran, dioxan or diethylene glygol dimethylether. So as to enhance yield and throughput, preferred solvents are methanol, water or tetrahydrofuran, and more preferably are water or tetrahydrofuran, especially water and tetrahydrofuran as solvent. Dioxan and diethylene glygol dimethylether are also preferred solvents which may optionally (and preferably) be employed together with water. Preferably, the solvent will be present in an amount of between 3 and 10 vol relative to the amount of the starting material (1 wt.), more preferably between 4 and 6 vol., especially 5 vol. Preferably the oxidising agent is present in an amount of 1–9 molar equivalents relative to the amount of the starting material. For example, when a 50% w/w aqueous solution of periodic acid is employed, the oxidising agent may be present in an amount of between 1.1 and 10 wt. relative to the amount of the starting material (1 wt.), more preferably between 1.1 and 3 wt., especially 1.3 wt. Preferably, the oxidation step will comprise the use of a chemical oxidising agent. More preferably, the oxidising agent will be periodic acid or iodic acid or a salt thereof. Most preferably, the oxidising agent will be periodic acid or sodium periodate, especially periodic acid. Alternatively (or in addition), it will also be appreciated that the oxidation step may comprise any suitable oxidation reaction, eg one which utilises air and/or oxygen. When the oxidation reaction utilises air and/or oxygen, the solvent used in said reaction will preferably be methanol. Preferably, step (a) will involve incubating the reagents at room temperature or a little warmer, say around 25° C. eg for 2 hours. The compound of formula (IV) may be isolated by recrystallisation from the reaction mixture by addition of an anti-solvent. A suitable anti-solvent for compound of formula (IV) is water. Surprisingly we have discovered that it is highly desirable to control the conditions under which the compound of formula (IV) is precipitated by addition of anti-solvent eg water. When the recrystallisation is performed using chilled water (eg water/ice mixture at a temperature of 0–5° C.) although better anti-solvent properties may be expected we have found that the crystalline product produced is very voluminous, resembles a soft gel and is very difficult to filter. Without being limited by theory we believe that this low density product contains a large amount of solvated solvent within the crystal lattice. By contrast when conditions of around 10° C. or higher are used (eg around ambient temperature) a granular product of a sand like consistency which is very easily filtered is produced. Under these conditions, crystallisation typically commences after around 1 hour and is typically completed within a few hours (eg 2 hours). Without being limited by theory we believe that this granular product contains little or no solvated solvent within the crystal lattice.

Step (b) will typically comprise the addition of a reagent suitable for converting a carboxylic acid to a carbothioic acid eg using hydrogen sulphide gas together with a suitable coupling agent eg carbonyldiimidazole (CDI) in the presence of a suitable solvent eg dimethylformamide.

An alternative process for preparing a compound of formula (II) comprises treating a compound of formula (X) with a reagent suitable for converting a carboxylic acid to a carbothioic acid eg using hydrogen sulphide gas together with a suitable coupling agent such as CDI in the presence of a suitable solvent eg DMF. Compounds of formula (X) may be prepared by methodology analogous to that described herein.

An alternative process for preparing a compound of formula (I) or a solvate thereof comprises reacting a compound of formula (VI)

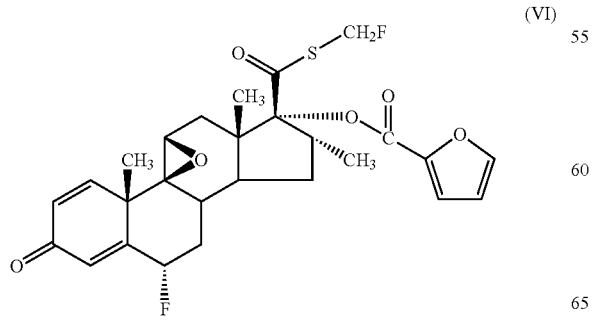

with a fluorine source.

Examples of suitable sources of fluorine include fluoride (eg sodium fluoride) or, more preferably, HF. The preferred reagent is aqueous HF. A solvent such as THF or DMF may be employed.

A compound of formula (VI) may be prepared by a process comprising (a) alkylating a compound of formula (VII)

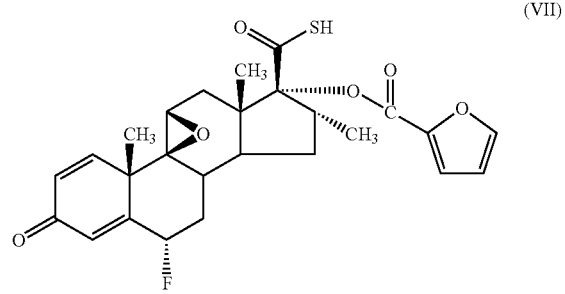

or a salt thereof;

(b) reacting a compound of formula (VIII)

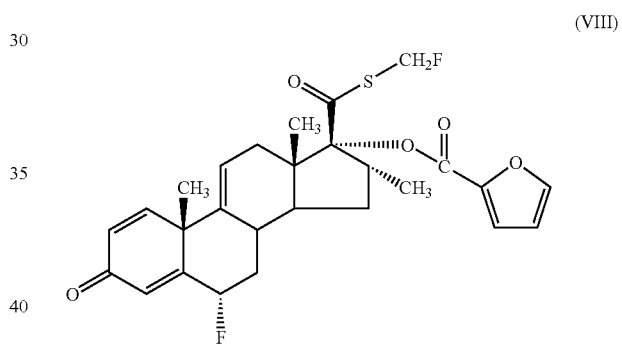

with an epoxide forming reagent; or (c) esterifying a compound of formula (IX)

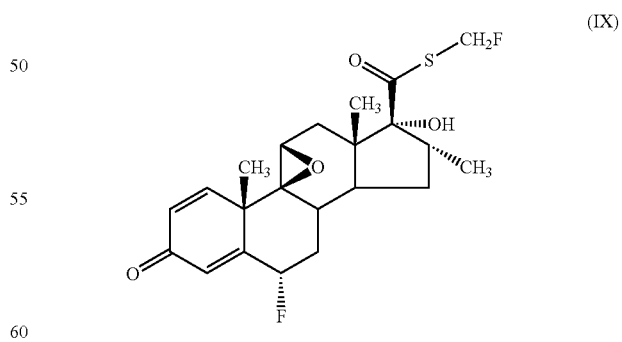

In process (a), analogous conditions to those described above for the conversion of a compound of formula (II) to a compound of formula (I) may be employed. Typically compound of formula (VII) will be reacted with a compound of formula FCH$_2$L wherein L represents a leaving group (eg a halogen atom, a mesyl or tosyl group or the like) for example, an appropriate fluoromethyl halide under standard conditions. Preferably, the fluoromethyl halide reagent is bromofluoromethane.

Process (b) is preferably performed in two steps: (i) formation of a halohydrin especially a bromohydrin (eg by reaction with bromodan or equivalent reagent), followed by (ii) treatment with base such as sodium hydroxide so as to effect ring closure. The product of step (i) is a compound of formula (IXA) which is a novel intermedate that may be isolated, if desired:

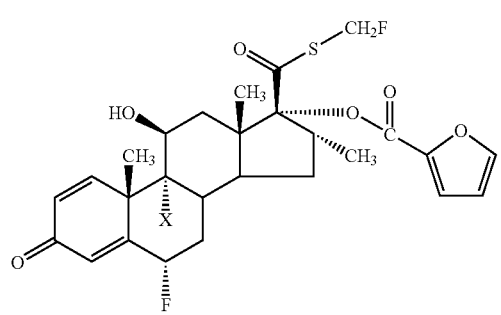

(IXA)

wherein X represents halogen, especially Br.

In process (c), a suitable reagent would be an activated derivative of 2-furoic acid such as an activated ester or preferably a 2-furoyl halide eg 2-furoyl chloride in the presence of an organic base eg triethylamine. This reaction may be performed at elevated temperature eg around 60° C. or else at ambient temperature in the presence of an acylation catalyst eg dimethylamino pyridine (DMAP).

Compounds of formula (VII) may be prepared by a process comprising esterification of a compound of formula (XI)

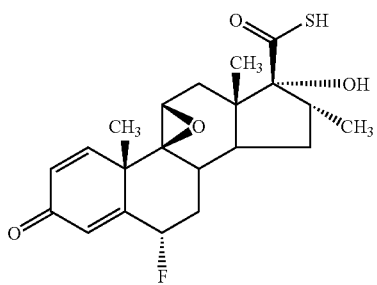

(XI)

Analogous conditions to those described above for the conversion of a compound of formula (III) to a compound of formula (II) may be employed. For example, a suitable reagent would be an activated derivative of 2-furoic acid such as an activated ester or preferably a 2-furoyl halide eg 2-furoyl chloride in the presence of an organic base eg triethylamine. Compound of formula (XI) is known (J Labelled Compd Radiopharm (1997) 39(7) 567–584).

A compound of formula (VIII) may be prepared by a process comprising
(a) alkylating a compound of formula (XII)

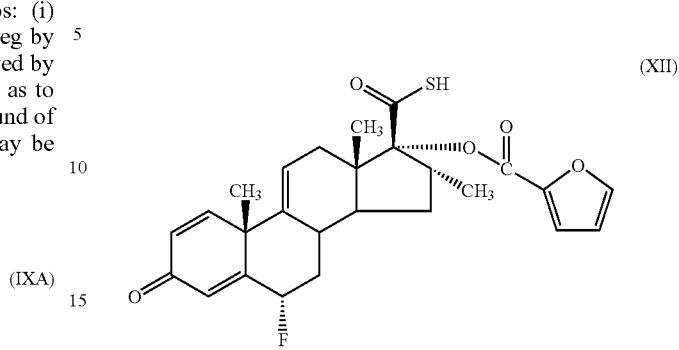

(XII)

or a salt thereof; or
(b) esterifying a compound of formula (XIII)

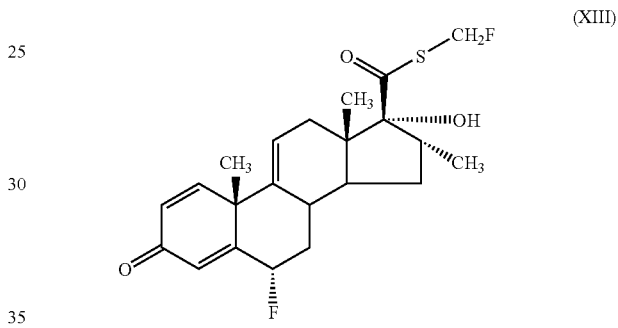

(XIII)

In process (a), analogous conditions to those described above for the conversion of a compound of formula (II) to a compound of formula (I) may be employed. Typically compound of formula (XII) will be reacted with a compound of formula $FCH_2L$ wherein L represents a leaving group (eg a halogen atom, a mesyl or tosyl group or the like) for example, an appropriate fluoromethyl halide under standard conditions. Preferably, the fluoromethyl halide reagent is bromofluoromethane.

In process (b), analogous conditions to those employed above for the conversion of a compound of formula (IX) to a compound of formula (VI) may be employed. For example, a suitable reagent would be an activated derivative of 2-furoic acid such as an activated ester or preferably a 2-furoyl halide eg 2-furoyl chloride in the presence of an organic base eg triethylamine.

Compounds of formula (IX) and (XIII) may be prepared by alkylating the corresponding thioacids (XI) and (XIV) (defined below) using methodology analogous to that already described (eg by reaction with a compound of formula $FCH_2L$ wherein L represents a leaving group (eg a halogen atom, a mesyl or tosyl group or the like) for example, an appropriate fluoromethyl halide under standard conditions. Preferably, the fluoromethyl halide reagent is bromofluoromethane. The thioacid (XI) is a known compound (J Labelled Compd Radiopharm (1997) 39(7) 567–584).

Compound of formula (XII) may be prepared by a process comprising esterifying a compound of formula (XIV):

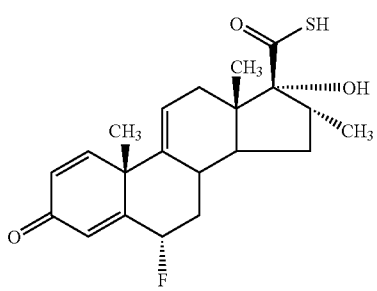

(XIV)

or a salt thereof.

This process may be performed using methodology analogous to that already described. For example, a suitable reagent would be an activated derivative of 2-furoic acid such as an activated ester or preferably a 2-furoyl halide eg 2-furoyl chloride in the presence of an organic base eg triethylamine.

Compounds of formula (XIV) may be prepared from the corresponding carboxylic acid eg by a process analogous to that described above for the conversion of a compound of formula (IV) to a compound of formula (III). The aforesaid corresponding carboxylic acid is known (Upjohn, WO 90/15816).

A further alternative process for preparing a compound of formula (I) or a solvate thereof comprises deprotecting or unmasking a compound of formula (I) in which the 11-β-hydroxy group is protected or masked. A first such process comprises deprotecting a compound of formula (XV)

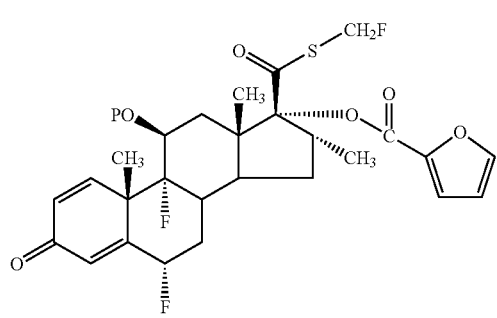

(XV)

wherein P represents a hydroxy protecting group.

Examples of hydroxy protecting groups P are described in Protective Groups in Organic Chemistry Ed JFW McOmie (Plenum Press 1973) or Protective Groups in Organic Synthesis by Theodora W Green (John Wiley and Sons, 1991).

Examples of suitable hydroxy protecting groups P include groups selected from carbonate, alkyl (eg t-butyl or methoxymethyl), aralkyl (eg benzyl, p-nitrobenzyl, diphenylmethyl or triphenylmethyl), heterocyclic groups such as tetrahydropyranyl, acyl (eg acetyl or benzyl) and silyl groups such as trialkylsilyl (eg t-butyldimethylsilyl). The hydroxy protecting groups may be removed by conventional techniques. Thus, for example, carbonate may be removed by treatment with base and alkyl, silyl, acyl and heterocyclic groups may be removed by solvolysis eg by hydrolysis under acid or basic conditions. Aralkyl groups such as triphenylmethyl may similarly be removed by solvolysis eg by hydrolysis under acidic conditions. Aralkyl groups such as benzyl or p-nitrobenzyl may be cleaved by hydrogenolysis in the presence of a Noble metal catalyst such as palladium on charcoal. p-Nitrobenzyl may also be cleaved by photolysis.

The 11-β-hydroxy group may be masked as a carbonyl group. Thus a second such process comprises reduction of a compound of formula (XVI)

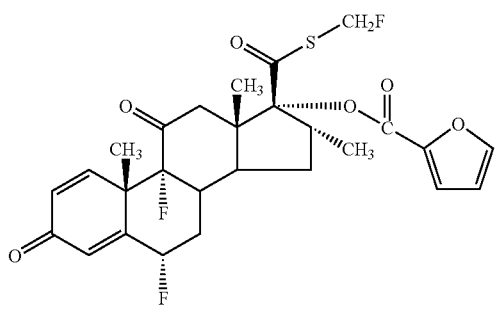

(XVI)

Reduction to the compound of formula (I) may be achieved eg by treatment with a hydride reducing agent such as borohydride eg sodium borohydride.

The 11-ketone (XVI) may also be masked. Examples of masked derivatives of compound of formula (XVI) include (i) ketal derivatives eg ketals formed by treatment of the compound of formula (XVI) with an alcohol eg methanol, ethanol or ethan-1,2-diol, (ii) dithioketal derivatives eg dithioketals formed by treatment of the compound of formula (XVI) with a thiol eg methanethiol, ethanethiol or ethan-1,2-dithiol, (iii) monothioketal derivatives eg monothioketals formed by treatment of the compound of formula (XVI) with eg 1-hydroxy-ethane-2-thiol, (iv) derivatives formed by treatment of the compound of formula (XVI) with an alcoholamine eg ephedrine, (v) imines formed by treatment of the compound of formula (XVI) with amines, (vi) oximes formed by treatment of compounds of formula (XVI) with hydroxylamines. We claims such derivatives of compound of formula (XVI) as an aspect of the invention.

These masked derivatives may be converted back to the ketone by conventional means eg ketals, imines and oximes are converted to carbonyl by treatment with dilute acid and dithioketals are converted to the ketone by a variety of methods as described by P. C. Bulman Page et al (1989), Tetrahedron, 45, 7643–7677 and references therein.

Compounds of formula (XV) may be prepared by a process comprising
(a) alkylating a compound of formula (XVII)

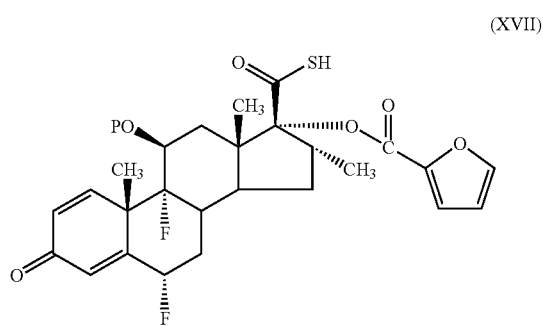

(XVII)

or a salt thereof wherein P represents a hydroxy protecting group; or (b) esterifying a compound of formula (XVIII)

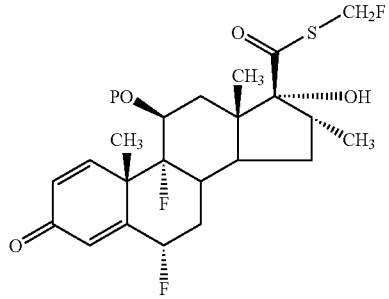

In step (a), analogous conditions to those described above for the conversion of a compound of formula (II) to a compound of formula (I) may be employed. Typically compound of formula (XVII) will be reacted with a compound of formula FCH$_2$L wherein L represents a leaving group (eg a halogen atom, a mesyl or tosyl group or the like) for example, an appropriate fluoromethyl halide under standard conditions. Preferably, the fluoromethyl halide reagent is bromofluoromethane.

In step (b), analogous conditions to those employed above for the conversion of a compound of formula (IX) to a compound of formula (VI) may be employed. For example, a suitable reagent would be an activated derivative of 2-furoic acid such as an activated ester or preferably a 2-furoyl halide eg 2-furoyl chloride in the presence of an organic base eg triethylamine.

Compound of formula (XVIII) may be prepared by alkylating the corresponding thioacid using methodology analogous to that already described (eg by reaction with a compound of formula FCH$_2$L wherein L represents a leaving group (eg a halogen atom, a mesyl or tosyl group or the like) for example, an appropriate fluoromethyl halide under standard conditions. Preferably, the fluoromethyl halide reagent is bromofluoromethane. The corresponding thioacids are known compounds or may be prepared by standard methodology. Compound of formula (XVIII) may alternatively be prepared by protection of the corresponding hydroxy derivative.

Compound of formula (XVII) may be prepared by a process comprising esterifying a compound of formula (XIX)

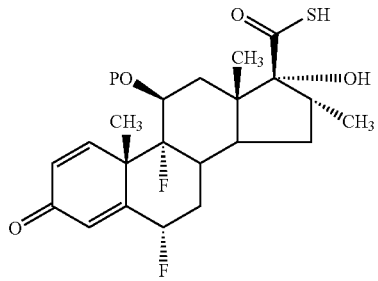

or a salt thereof wherein P represents a hydroxy protecting group.

This process may be performed using methodology analogous to that already described for the conversion of compounds of formula (III) to (II). For example, a suitable reagent would be an activated derivative of 2-furoic acid such as an activated ester or preferably a 2-furoyl halide eg 2-furoyl chloride in the presence of an organic base eg triethylamine.

Compounds of formula (XIX) may be prepared by protecting the corresponding hydroxy derivative (III), having first protected the thioacid which would then be deprotected.

Compounds of formula (XVI) may be prepared by a process comprising (a) alkylating a compound of formula (XX)

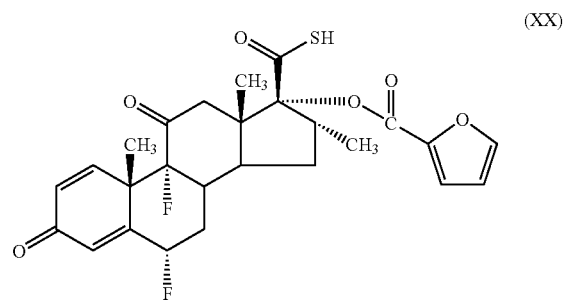

or a salt thereof or a derivative wherein the 11-carbonyl group is masked; or (b) esterifying a compound of formula (XXI)

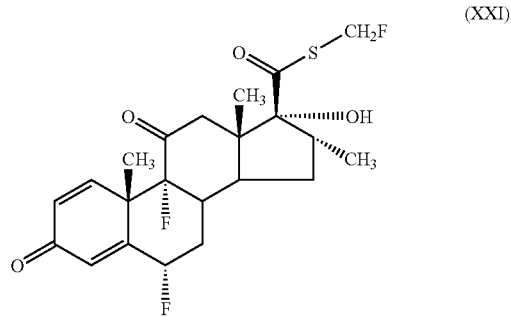

or a derivative wherein the 11-carbonyl group is masked.

In step (a), analogous conditions to those described above for the conversion of a compound of formula (III) to a compound of formula (II) may be employed. Typically compound of formula (XX) will be reacted with a compound of formula FCH$_2$L wherein L represents a leaving group (eg a halogen atom, a mesyl or tosyl group or the like) for example, an appropriate fluoromethyl halide under standard conditions. Preferably, the fluoromethyl halide reagent is bromofluoromethane.

In step (b), analogous conditions to those employed above for the conversion of a compound of formula (IX) to a compound of formula (VI) may be employed. For example, a suitable reagent would be an activated derivative of 2-furoic acid such as an activated ester or preferably a 2-furoyl halide eg 2-furoyl chloride in the presence of an organic base eg triethylamine.

Compound of formula (XXI) or a derivative thereof wherein the 11-ketone group is masked may be prepared by alkylating the corresponding thioacid using methodology analogous to that already described (eg by reaction with a compound of formula FCH$_2$L wherein L represents a leaving group (eg a halogen atom, a mesyl or tosyl group or the like) for example, an appropriate fluoromethyl halide under standard conditions. Preferably, the fluoromethyl halide reagent is bromofluoromethane. The corresponding thioacids are known compounds or may be prepared from the corresponding carboxylic acids by methods analogous to those previously described.

Compound of formula (XX) may be prepared by a process comprising esterifying a compound of formula (XXII)

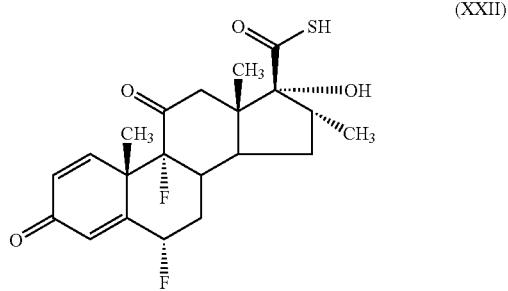

(XXII)

or a derivative thereof wherein the 11-ketone group is masked.

This process may be performed using methodology analogous to that already described. For example, a suitable reagent would be an activated derivative of 2-furoic acid such as an activated ester or preferably a 2-furoyl halide eg 2-furoyl chloride in the presence of an organic base eg triethylamine.

Compounds of formula (XXII) and derivatives thereof wherein the 11-ketone is masked may be prepared by oxidation of the corresponding hydroxy derivative (IV) followed by masking of the ketone and subsequent conversion of the carboxylic acid group to the thioacid (see eg conversion of compounds of formula (IV) to (III).

A further alternative process for the preparation of compounds of formula (I) or a solvate thereof comprises reaction of a compound of formula (XXIII)

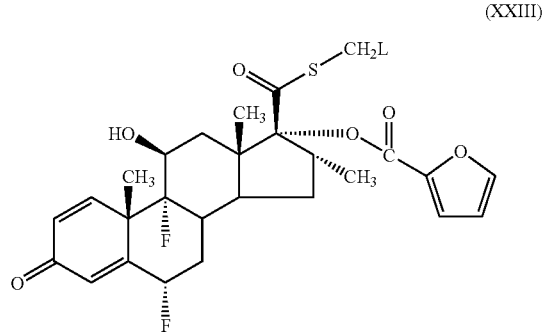

(XXIII)

wherein L represents a leaving group (eg halide other than fluoride such as chloride, iodide or a sulphonate ester such mesylate, tosylate, triflate) with a fluorine source.

Preferably the fluorine source is fluoride ion eg KF. Further details for this conversion may be obtained by reference to G. H. Phillipps et al., (1994) Journal of Medicinal Chemistry, 37, 3717–3729 or J Labelled Compd Radiopharm (1997) 39(7) 567–584).

Compounds of formula (XXIII) may be prepared by methods analogous to those described herein. Corresponding novel intermediates of formula (VI), (VIII), (IX), (IXA), (XV) and (XVI) wherein the —CH2F moiety is replaced with a —CH2L moiety (wherein L represents a leaving group other than fluorine) are claimed as an aspect of the invention.

A further alternative process for the preparation of compounds of formula (I) or a solvate thereof comprises deprotection or unmasking of a derivative of a compound of formula (I) in which the 3-carbonyl group is protected or masked.

The 3-carbonyl group may be masked in a manner analogous to that described above in relation to masking of the 11-carbonyl position. Thus the 3-carbonyl may be masked eg as a ketal, monothioketal, dithioketal, derivative with an alcoholamine, oxime or imine. The carbonyl group may be recovered by conventional means eg ketals are converted to carbonyl by treatment with dilute acid and dithioketals are converted to the ketone by a variety of methods as described by P. C. Bulman Page et al (1989), Tetrahedron, 45, 7643–7677 and references therein.

Certain intermediate compounds are new and we provide these, together where appropriate with their salts and solvates, as an aspect of the invention.

As noted above, we provide as a particular aspect of the invention a process for preparing a compound of formula (I) in unsolvated form which comprises:
(a) Crystallising the compound of formula (I) in the presence of a non-solvating solvent such as ethanol, methanol, water, ethyl acetate, toluene, methylisobutylketone or mixtures thereof; or
(b) Desolvating a compound of formula (I) in solvated form (eg in the form of a solvate with acetone, isopropanol, methylethylketone, DMF or tetrahydrofuran) eg by heating.

In step (b) the desolvation will generally be performed at a temperature exceeding 50° C. preferably at a temperature exceeding 100° C. Generally heating will be performed under vacuum.

There is also provided a compound of formula (I) in unsolvated form obtainable by the aforementioned process.

There is also provided as a particular aspect of the invention a process for preparing a compound of formula (I) as unsolvated Form 1 polymorph which comprises dissolving compound of formula (I) in methylisobutylketone, ethyl acetate or methyl acetate and producing compound of formula (I) as unsolvated Form 1 by addition of a non-solvating anti-solvent such as iso-octane or toluene.

According to a first preferred embodiment of this process the compound of formula (I) may be dissolved in ethyl acetate and compound of formula (I) as unsolvated Form 1 polymorph may be obtained by addition of toluene as anti-solvent. In order to improve the yield, preferably the ethyl acetate solution is hot and once the toluene has been added the mixture is distilled to reduce the content of ethyl acetate.

According to a second preferred embodiment of this process the compound of formula (I) may be dissolved in methylisobutylketone and compound of formula (I) as unsolvated Form 1 polymorph may be obtained by addition of isooctane as anti-solvent There is also provided a compound of formula (I) as unsolvated Form 1 polymorph obtainable by the aforementioned processes.

A process for preparing a compound of formula (I) as unsolvated Form 2 polymorph comprises dissolving compound of formula (I) in unsolvated form in methanol or dry dichloromethane and recrystallising the compound of formula (I) as unsolvated Form 2 polymorph. Typically the compound of formula (I) will be dissolved in hot in methanol or dry dichloromethane and allowed to cool.

There is also provided a compound of formula (I) as unsolvated Form 2 polymorph obtainable by the aforementioned process.

A process for preparing a preparing a compound of formula (I) as unsolvated Form 3 polymorph comprises dissolving compound of formula (I) or a solvate thereof (in particular as the acetone solvate) in dichloromethane in the presence of water (typically 1–3% water by volume) and recrystallising the compound of formula (I) as unsolvated Form 3 polymorph.

There is also provided a compound of formula (I) as unsolvated Form 3 polymorph obtainable by the aforementioned process.

The advantages of the compound of formula (I) and/or its solvates or polymorphs may include the fact that the substance appears to demonstrate excellent anti-inflammatory properties, with predictable pharmacokinetic and pharmacodynamic behaviour, with an attractive side-effect profile and is compatible with a convenient regime of treatment in human patients. Further advantages may include the fact that the substance has desirable physical and chemical properties which allow for ready manufacture and storage.

DETAILED DESCRIPTION OF THE INVENTION

The following non-limiting Examples illustrate the invention:

EXAMPLES

General $^1$H-nmr spectra were recorded at 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), ddd (doublet of doublet of doublets), dt (doublet of triplets) and b (broad). Biotage refers to prepacked silica gel cartridges containing KP-Sil run on flash 12i chromatography module. LCMS was conducted on a Supelcosil LCABZ+ PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0–0.7 min 0% B, 0.7–4.2 min 100% B, 4.2–5.3 min 0% B, 5.3–5.5 min 0% B at a flow rate of 3 ml/min. The mass spectra were recorded on a Fisons VG Plafform spectrometer using electrospray positive and negative mode (ES+ve and ES−ve).

DSC and TGA profiles were obtained using a Netzsch STA449C simultaneous thermal analyser using an unsealed pan with nitrogen gas flow and a thermal gradient of 10° C./min.

The moisture sorption characteristics were obtained using a Hiden Igasorb water sorption microbalance. The programme provides for stepwise increase in relative humidity (RH) from 0 to 90% RH and then decrease back to 0% RH in steps of 10% RH.

Figure 1:
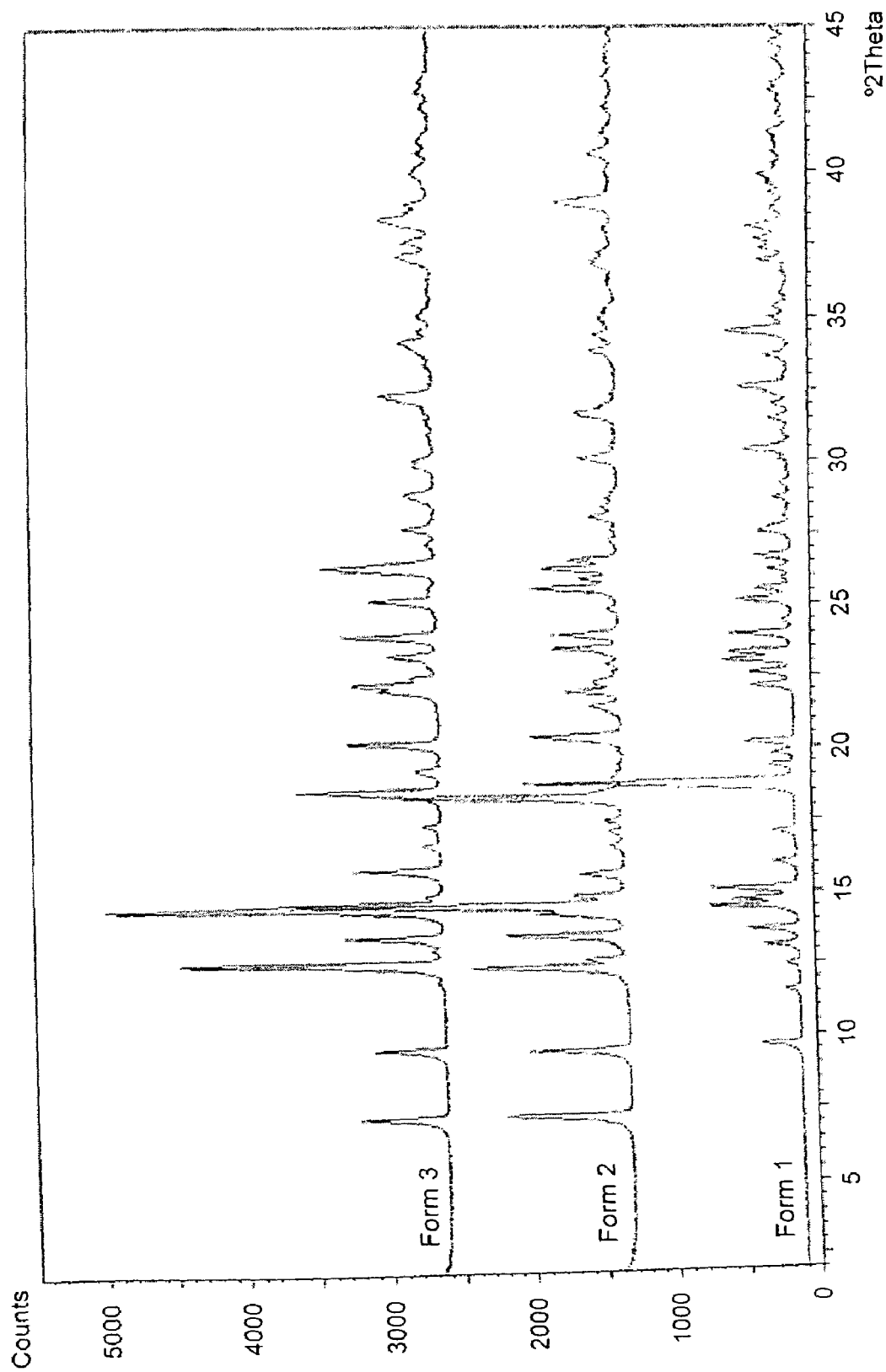
FIG. 1: Overlay of the XRPD profiles of Form 1, Form 2 and Form 3 polymorphs of unsolvated Compound of formula (I)
Figure 2:
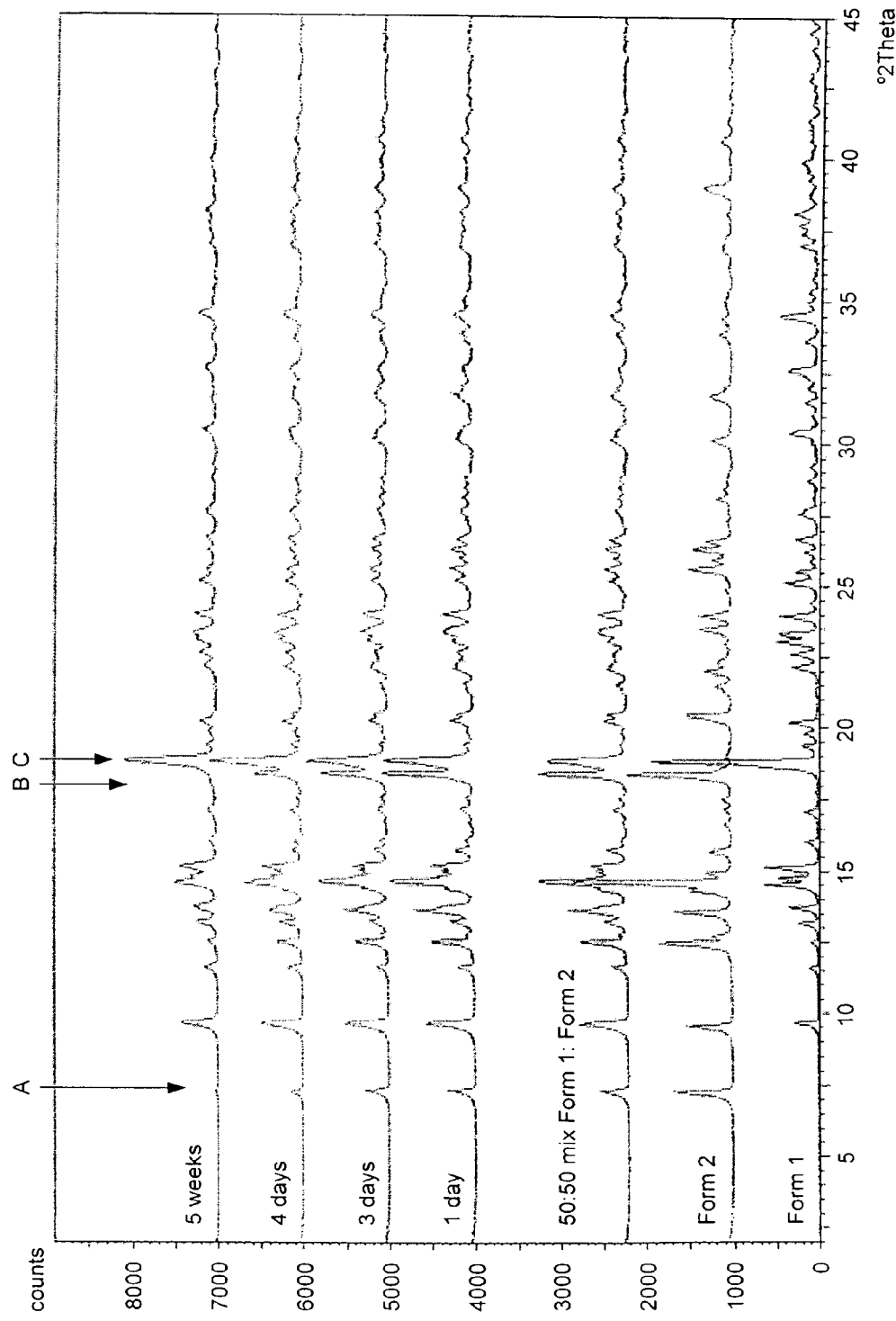
FIG. 2: Overlay of the XRPD profiles of Form 1, Form 2 and a 50:50 mixture of Form 1 and Form 2 polymorphs of unsolvated Compound of formula (I) together with the time dependence of the profile of the 50:50 mixture of Form 1 and Form 2

The XRPD analysis shown in FIG. 1 and 2 were performed on a Phillips X'pert MPD powder diffractometer, Ser. No. DY667. The method runs from 2 to 45 degrees 2Theta with 0.02 degree 2Theta step size and a 1 second collection time at each step. The XRPD analysis shown in FIG. 4 employed the same instrument with an Anton Parr TTK thermal accessory using a method running from 2 to 35 degrees 2Theta with 0.04 degree 2Theta step size and a 1 second collection time.

Intermediates

Intermediate 1: 6α, 9α-Difluoro-17α-[(2-furanylcarbonyl)oxy]-11β-hydroxy-16α-methyl-3-oxo-androsta-1, 4-diene-17β-carbothioic acid A solution of 6α, 9α-difluoro-11β, 17α-dihydroxy-16α-methyl-3-oxo-androsta-1,4-diene-17β-carbothioic acid (prepared in accordance with the procedure described in GB 2088877B) (18 g, 43.64 mmol) in anhydrous dichloromethane (200 ml) and triethylamine (15.94 ml, 114 mmol) was treated at <5° C. with a solution of 2-furoyl chloride (11.24 ml, 114 mmol) in anhydrous dichloromethane (100 ml) over approximately 40 min. The solution was stirred at <5° C. for 30 min. The resulting solid was collected by filtration, washed successively with 3.5% aqueous sodium hydrogen carbonate solution, water, 1M hydrochloric acid, and water and dried in vacuo at 60° C. to give a cream coloured solid. The dichloromethane filtrate was washed successively with 3.5% sodium hydrogen carbonate solution, water, 1 M hydrochloric acid, water, dried ($Na_2SO_4$) and evaporated to give a cream coloured solid which was combined with that isolated above. The combined solids (26.9 g) were suspended in acetone (450 ml) and stirred. Diethylamine (16.8 ml, 162 mmol) was added and the mixture stirred at room temperature for 4.5 h. The mixture was concentrated and the precipitate collected by filtration and washed with a little acetone. The washings and filtrate were combined, concentrated and loaded onto a silica gel Biotage column which was eluted with 24:1 chloroform:methanol. Fractions which contained the more polar component were combined and evaporated to give a cream coloured solid. This was combined with the solid isolated above and dried in vacuo to give a pale beige coloured solid (19.7 g). This was dissolved in warm water, the pH adjusted to 2 with concentrated hydrochloric acid and the mixture extracted with ethyl acetate. The organic extract was dried ($Na_2SO_4$) and evaporated to give, after drying at 50° C., the title compound as a cream coloured solid (18.081 g, 82%): LCMS retention time 3.88 min, m/z 507 MH$^+$, NMR δ ($CDCl_3$) includes 7.61 (1H, m), 7.18–7.12 (2H, m), 6.52 (1H, dd, J 4, 2 Hz), 6.46 (1H, s), 6.41 (1H, dd, J 10, 2 Hz), 5.47 and 5.35 (1H, 2m), 4.47 (1H, bd, J 9 Hz), 3.37 (1H, m), 1.55 (3H, s), 1.21 (3H, s), 1.06 (3H, d, J 7 Hz).

Intermediate 1:6α, 9α-Difluoro-17α-[(2-furanylcarbonyl)oxy]-11β-hydroxy-16α-methyl-3-oxo-androsta-1, 4-diene-17β-carbothioic acid (first alternative method)

A stirred suspension of 6α, 9α-difluoro-11β, 17α-dihydroxy-16α-methyl-3-oxo-androsta-1,4-diene-17β-carbothioic acid (prepared in accordance with the procedure described in GB 2088877B) (1 wt, 49.5 g) in acetone (10 vol) is cooled to 0–5° C. and treated with triethylamine (0.51 wt, 2.1 eq), keeping the temperature below 5° C., and stirred for 5 min at 0–5° C. 2-Furoyl chloride (0.65 wt, 2.05 eq) is then added over a minimum of 20 min, maintaining a reaction temperature at 0–5° C. The reaction is stirred for 30 min at 0–5° C. then sampled for analysis by HPLC. A solution of diethanolamine (1.02 wt, 4 eq) in methanol (0.8 vol) is added over ca 15 min followed by a line wash of methanol (0.2 vol) and the reaction stirred at 0–5° C. for 1 h. The reaction is again sampled for analysis by HPLC then warmed to approximately 20° C. and treated with water (1.1 wt). The reaction mixture is then treated with a solution of HCl (SG1.18 (11.5M), 1 vol) in water (10 vol) over ca 20 min maintaining a reaction temperature below 25° C. The suspension is stirred at 20–23° C. for at least 30 minutes then filtered. The filter cake is washed with water (3×2 vol). The product is dried in vacuo at approximately 60° C. overnight to give the title compound as a white solid (58.7 g, 96.5%).

Intermediate 1: 6α, 9α-Difluoro-17α-[(2-furanylcarbonyl)oxy]-11β-hydroxy-16α-methyl-3-oxo-androsta-1,4-diene-17β-carbothioic acid (second alternative method)

A stirred suspension of 6α, 9α-difluoro-11β, 7α-dihydroxy-16α-methyl-3-oxo-androsta-1,4-diene-17β-carbothioic acid (prepared in accordance with the procedure described in GB 2088877B) (1 wt, 49.5 g) in acetone (10 vol) is cooled to 0–5° C. and treated with triethylamine (0.51 wt, 2.1 eq), keeping the temperature below 5° C., and stirred for 5 min at 0–5°. 2-Furoyl chloride (0.65 wt, 2.05 eq) is then added over a minimum of 20 min, maintaining a reaction temperature at 0–5° C. The reaction mixture is stirred for at least 30 minutes and diluted with water (10 vol) maintaining a reaction temperature in the range 0–5° C. The resultant precipitate is collected by filtration and washed sequentially with acetone/water (50/50 2 vol) and water (2×2 vol). The product is dried under vacuum at approximately 55° C. overnight to leave 6α,9α-difluoro-17α-[(2-furanylcarbonyl)oxy]-11β-hydroxy-16α-methyl-3-oxo-androsta-1,4-diene-17β-yl S-(2-furanylcarbonyl) thioanhydride as a white solid (70.8 g, 98.2%) (NMR δ (CD$_3$CN) 0.99 (3H, d) (J=7.3 Hz), 1.24 (3H, s), 1.38 (1 H, m) (J=3.9 Hz), 1.54 (3H, s), 1.67 (1H, m), 1.89 (1H, broad d) (J=15.2 Hz), 1.9–2.0 (1H, m), 2.29–2.45 (3H, m), 3.39 (1H, m), 4.33 (1H, m), 4.93 (1H, broad s), 5.53 (1H, ddd) (J=6.9,1.9 Hz; J$_{HF}$=50.9 Hz), 6.24 (1H, m), 6.29 (1H, dd) (J=10.3, 2.0 Hz), 6.63 (2H, m), 7.24–7.31 (3H, m), 7.79 (1 H, dd) (J=<1 Hz), 7.86 (1H, dd) (J=<1 Hz)).

6α,9α-difluoro-17α-[(2-furanylcarbonyl)oxy]-11β-hydroxy-16α-methyl-3-oxo-androsta-1,4-diene-17β-yl S-(2-furanylcarbonyl) thioanhydride (0.56 g) is mixed with 6α, 9α-difluoro-11β, 17α-dihydroxy-16α-methyl-3-oxo-androsta-1,4-diene-17β-carbothioic acid (0.41 g) in a 1:1 molar ratio in DMF (10 volumes wrt total steroid input). The reaction mixture is treated with triethylamine (approximately 2.1 equivalents) and the mixture is stirred at approximately 20° C. for approximately 6 hours. Water (50 vol) containing excess conc HCl (0.5 vol) is added to the reaction mixture and the resultant precipitate collected by filtration. The bed is washed with water (2×5 vol) and dried in vacuo at approximately 55° C. overnight to leave the title compound as a white solid (0.99 g,102%).

Intermediate 1A: 6α, 9α-Difluoro-17α-[(2-furanylcarbonyl)oxy]-11β-hydroxy-16α-methyl-3-oxo-androsta-1,4-diene-17β-carbothioic acid diisopropylethylamine salt A stirred suspension of 6α, 9α-difluoro-11β, 17α-dihydroxy-16α-methyl-3-oxo-androsta-1,4-diene-17β-carbothioic acid (prepared in accordance with the procedure described in GB 2088877B) (49.5 g) in methylacetate (500 ml) is treated with triethylamine (35 ml) maintaining a reaction temperature in the range 0–5° C. 2-Furoyl chloride (25 ml) is added and the mixture stirred at 0–5° C. for 1 hour. A solution of diethanolamine (52.8 g) in methanol (50 ml) is added and the mixture stirred at 0–5° C. for at least 2 hours. Dilute hydrochloric acid (approx 1 M, 550 ml) is added maintaining a reaction temperature below 15° C. and the mixture stirred at 15° C. The organic phase is separated and the aqueous phase is back extracted with methyl acetate (2×250 ml). All of the organic phases are combined, washed sequentially with brine (5×250 ml) and treated with diisopropylethylamine (30 ml). The reaction mixture is concentrated by distillation at atmospheric pressure to an approximate volume of 250 ml and cooled to 25–30° C. (crystallisation of the desired product normally occurs during distillation/subsequent cooling). Tertiary butyl methyl ether (TBME) (500 ml) is added, the slurry further cooled and aged at 0–5° C. for at least 10 minutes. The product is filtered off, washed with chilled TBME (2×200 ml) and dried under vacuum at approximately 40–50° C. (75.3 g, 98.7%). NMR (CDCl$_3$) δ: 7.54–7.46 (1H, m), 7.20–7.12 (1H, dd), 7.07–6.99 (1H, dd), 6.48–6.41 (2H, m), 6.41–6.32 (1H, dd), 5.51–5.28 (1 H, dddd $^2$J$_{H-F}$ 50 Hz), 4.45–4.33(1 H, bd), 3.92–3.73 (3H, bm), 3.27–3.14 (2H, q), 2.64–2.12 (5H, m), 1.88–1.71 (2H, m), 1.58–1.15 (3H, s), 1.50–1.38 (15H, m), 1.32–1.23 (1H, m), 1.23–1.15 (3H s), 1.09–0.99 (3H, d)

Intermediate 1B: 6α, 9α-Difluoro-17α-[(2-furanylcarbonyl)oxy]-11β-hydroxy-16α-methyl-3-oxo-androsta-1,4-diene-17β-carbothioic acid triethylamine salt A stirred suspension of Intermediate 1 (30 g) in ethylacetate (900 ml) is treated with triethylamine (1.05 molar equivalents, 8.6 ml) and the mixture is stirred at approximately 20° C. for 1.5 hours. The precipitate is filtered off, washed with ethylacetate (2×2 vol) and dried in vacuo at 45° C. for 18 hours to give title compound as a white solid (28.8 g, 80%). NMR (CDCl$_3$) δ: 7.59–7.47 (1H, m), 7.23–7.13 (1H, dd), 7.08–6.99 (1H, d), 6.54–6.42 (2H, m), 6.42–6.32 (1H, dd), 5.55–5.26 (1H, dddd $^2$J$_{H-F}$ 50 Hz), 4.47–4.33 (1H, bd), 3.88–3.70 (1H, bm), 3.31–3.09 (6H, q), 2.66–2.14 (5H, m), 1.93–1.69 (2H, m), 1.61–1.48 (3H, s), 1.43–1.33 (9H, t), 1.33–1.26 (1H, m), 1.26–1.15 (3H s), 1.11–0.97 (3H, d).

EXAMPLES

Example 1

6α, 9α-Difluoro-17α-[(2-furanylcarbonyl)oxy]-11β-hydroxy-16α-methyl-3-oxo-androsta-1,4-diene-17β-carbothioic acid S-fluoromethyl ester Unsolvated Form 1

A suspension of Intermediate 1 (2.5 g, 4.94 mmol) was dissolved in anhydrous N, N-dimethylformamide (25 ml) and sodium hydrogen carbonate (465 mg, 5.53 mmol) was added. The mixture was stirred at −20° C. and bromofluoromethane (0.77 ml, 6.37 mmol) was added and the mixture was stirred at −20° C. for 2 h. Diethylamine (2.57 ml, 24.7 mmole) was added and the mixture stirred at −20° C. for 30 min. The mixture was added to 2M hydrochloric acid (93 ml) and stirred for 30 min. Water (300 ml) was added and the precipitate was collected by filtration, washed with water and dried in vacuo at 50° C. to give a white solid which was recrystallised from acetone/water (to yield the acetone solvate of 6α, 9α-difluoro-17α-[(2-furanylcarbonyl)oxy]-11β-hydroxy-16α-methyl-3-oxo-androsta-1,4-diene-17α-carbothioic acid S-fluoromethyl ester) and dried in vacuo at 50° C. to give the title compound (2.351 g, 88%): LCMS retention time 3.66 min, m/z 539 MH$^+$, NMR δ (CDCl$_3$) includes 7.60 (1H, m), 7.18–7.11 (2H, m), 6.52 (1H, dd, J 4.2 Hz), 6.46 (1H, s), 6.41 (1 H, dd, J 10, 2 Hz), 5.95 and 5.82 (2H dd, J 51, 9 Hz), 5.48 and 5.35 (1H, 2m), 4.48 (1H, m), 3.48 (1H, m), 1.55 (3H, s), 1.16 (3H, s), 1.06 (3H, d, J 7Hz).

Pharmacological Activity

In Vitro Pharmacological Activity

Pharmacological activity was assessed in a functional in vitro assay of glucocorticoid agonist activity which is generally predictive of anti-inflammatory or anti-allergic activity in vivo.

For the experiments in this section, compound of formula (I) was used as unsolvated Form 1.

The functional assay was based on that described by K. P. Ray et al., Biochem J. (1997), 328, 707–715. A549 cells stably transfected with a reporter gene containing the NF-κB responsive elements from the ELAM gene promoter coupled to sPAP (secreted alkaline phosphatase) were treated with test compounds at appropriate doses for 1 hour at 37° C. The cells were then stimulated with tumour necrosis factor (TNF, 10 ng/ml) for 16 hours, at which time the amount of alkaline phosphatase produced is measured by a standard colourimetric assay. Dose response curves were constructed from which EC$_{50}$ values were estimated.

In this test the compound of Example 1 showed an EC$_{50}$ value of <1 nM.

The glucocorticoid receptor (GR) can function in at least two distinct mechanisms, by upregulating gene expression through the direct binding of GR to specific sequences in gene promotors, and by downregulating gene expression that is being driven by other transcription factors (such as NFκB or AP-1) through their direct interaction with GR.

In a variant of the above method, to monitor these functions, two reporter plasmids have been generated and introduced separately into A549 human lung epithelial cells by transfection. The first cell line contains the sPAP reporter gene under the control of a synthetic promoter that specifically responds to activation of the transcription factor NFκB when stimulated with TNFα. The second cell line contains the renilla luciferase reporter gene under the control of a synthetic promotor that comprises 3 copies of the consensus glucocorticoid response element (GRE), and which responds to direct stimulation by glucocorticoids. Measurement of transactivation and transrepression was conducted using these two cell lines in 96 well plate (40,000 cells per well) and growing overnight at 37° C. Test compounds were dissolved in DMSO, and added to the cells at a final DMSO concentration of 0.7%. After incubation for 1 h 0.5 ng/ml TNFα (R&D Systems) was added to the NFκB assay and after a further 15 hours at 37° C., the levels of sPAP and renilla luciferase were measured and dose response curves were constructed from which EC$_{50}$ values were determined.

|  | Transactivation (GR) ED$_{50}$ (nM) | Transrepression (NFκB) ED$_{50}$ (nM) |
| --- | --- | --- |
| Compound of Formula (I) | 0.06 | 0.20 |
| Metabolite (X) | >250 | >1000 |
| Fluticasone propionate | 0.07 | 0.16 |

In Vivo Pharmacological Activity

Pharmacological activity in vivo was assessed in an ovalbumin sensitised Brown Norway rat eosinophilia model. This model is designed to mimic allergen induced lung eosinophilia, a major component of lung inflammation in asthma.

For the experiments in this section, compound of formula (I) was used as unsolvated Form 1.

Compound (I) produced dose dependant inhibition of lung eosinophilia in this model after dosing as an intratracheal (IT) suspension in saline 30 min prior to ovalbumin challenge. Significant inhibition is achieved after a single dose of 30 μg of compound (1) and the response was significantly (p=0.016) greater than that seen with an equivalent dose of fluticasone propionate in the same study (69% inhibition with compound (I) vs 41% inhibition with fluticasone propionate).

In a rat model of thymus involution 3 daily IT doses of 100 μg of compound (I) induced significantly smaller reductions in thymus weight (p=0.004) than an equivalent dose of fluticasone propionate in the same study (67% reduction of thymus weight with compound (I) vs 78% reduction with fluticasone propionate).

Taken together these results indicate a superior therapeutic index for compound (I) compared to fluticasone propionate.

In vitro Metabolism in Rat and Human Hepatocytes

Incubation of compound (I) with rat or human hepatocytes shows the compound to be metabolised in an identical manner to fluticasone propionate with the 17-β carboxylic acid (X) being the only significant metabolite produced. Investigation of the rate of appearance of this metabolite on incubation of compound (I) with human hepatocytes (37° C., 10 μM drug concentration, hepatocytes from 3 subjects, 0.2 and 0.7 million cells/mL) shows compound (I) to be metabolised ca. 5-fold more rapidly than fluticasone propionate:

| Subject number | Cell density (million cells/mL) | 17-β acid metabolite production (pmol/h) | |
| --- | --- | --- | --- |
|  |  | Compound (I) | Fluticasone propionate |
| 1 | 0.2 | 48.9 | 18.8 |
| 1 | 0.7 | 73.3 | 35.4 |
| 2 | 0.2 | 118 | 9.7 |
| 2 | 0.7 | 903 | 23.7 |
| 3 | 0.2 | 102 | 6.6 |
| 3 | 0.7 | 580 | 23.9 |

Median metabolite production 102–118 pmol/h for compound (I) and 18.8–23.0 pmol/h for fluticasone propionate.

Pharmacokinetics After Intravenous (IV) and Oral Dosing in Rats

Compound (I) was dosed orally (0.1 mg/kg) and IV (0.1 mg/kg) to male Wistar Han rats and pharmacokinetic parameters determined. Compound (I) showed negligible oral bioavailability (0.9%) and plasma clearance of 47.3 mL/min/kg, approaching liver blood flow (plasma clearance of fluticasone propionate=45.2 mL/min/kg).

Pharmacokinetics After Intra-tracheal Dry Powder Dosing in the Pig.

Anaesthetised pigs (2) were dosed intra-tracheally with a homogenous mixture of compound (I) (1 mg) and fluticasone propionate (1 mg) as a dry powder blend in lactose (10% w/w). Serial blood samples were taken for up to 8 h following dosing. Plasma levels of compound (I) and fluticasone propionate were determined following extraction and analysis using LC-MS/MS methodology, the lower limits of quantitation of the methods were 10 and 20 µg/mL for compound (I) and fluticasone propionate respectively. Using these methods compound (I) was quantifiable up to 2 hours after dosing and fluticasone propionate was quantifiable up to 8 hours after dosing. Maximum plasma concentrations were observed for both compounds within 15 min after dosing. Plasma half-life data obtained from IV dosing (0.1 mg/kg) was used to calculate AUC (0-inf) values for compound (I). This compensates for the plasma profile of Compound (I) only being defined up to 2 hours after an IT dose and removes any bias due to limited data between compound (I) and fluticasone propionate.

$C_{max}$ and AUC (0-inf) values show markedly reduced systemic exposure to compound (I) compared to fluticasone propionate:

|  | Cmax (pg/mL) | | AUC (0–inf) (hr · pg/mL) | |
| --- | --- | --- | --- | --- |
|  | Pig 1 | Pig 2 | Pig 1 | Pig 2 |
| Compound of Formula (I) | 117 | 81 | 254 | 221 |
| Fluticasone propionate | 277 | 218 | 455 | 495 |

The pharmacokinetic parameters for both compound (I) and fluticasone propionate were the same in the anaesthetised pig following intravenous administration of a mixture of the two compounds at 0.1 mg/kg. The clearance of these two glucocorticoids is similar is this experimental pig model.

Example 1

6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester Unsolvated Form 1 (First Alternative Method)

A mobile suspension of Intermediate 1A (12.61 g, 19.8 mmol; equivalent to 10 g of Intermediate 1) in ethyl acetate (230 ml) and water (50 ml) is treated with a phase transfer catalyst (benzyltributylammonium chloride, 10 mol %), cooled to 3° C. and treated with bromofluoromethane (1.10 ml, 19.5 mmol, 0.98 equivalents), washing in with pre-chilled (0° C.) ethyl acetate (EtOAc) (20 ml). The suspension is stirred overnight, allowing to warm to 17° C. The aqueous layer is separated and the organic phase is sequentially washed with 1 M HCl (50 ml), 1% w/v NaHCO₃ solution (3×50 ml) and water (2×50 ml). The ethylacetate solution is distilled at atmospheric pressure until the distillate reaches a temperature of approximately 73° C. at which point toluene (150 ml) is added. Distillation is continued at atmospheric pressure until all remaining EtOAc has been removed (approximate distillate temperature 103° C.). The resultant suspension is cooled and aged at <10° C. and filtered off. The bed is washed with toluene (2×30 ml) and the product oven dried under vacuum at 60° C. to constant weight to yield the title compound (8.77 g, 82%)

Example 1

6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester Unsolvated Form 1 (Second Alternative Method)

A suspension of 6α, 9α-difluoro-17β-[(2-furanylcarbonyl)oxy]-11β-hydroxy-16α-methyl-3-oxo-androsta-1,4-diene-17β-carbothioic acid S-fluoromethyl ester acetone solvate (prepared eg according to Example 11) (50.0 g) in acetone (1500 ml) and water (75 ml) was heated to reflux. The resultant mixture was clarified by hot filtration (Whatman 54 filter paper) during which time some solid crystallised in the filtrate. Further acetone (200 ml) was added to the filtrate giving a bright solution at reflux. The solution was distilled at atmospheric pressure until turbidity was noted whilst at reflux (approx 750 ml solvent collected). Toluene (1000 ml) was added to the hot solution and distillation at atmospheric pressure was continued giving crystallisation at a temperature of approximately 98° C. Distillation of solvent was continued until a reaction temperature of 105° C. was achieved (approximately 945 ml solvent collected). The mixture was cooled to ambient temperature, further cooled and aged at <10° C. for 10 minutes. The product was filtered off, washed with toluene (150 ml) and sucked dry. The product was dried at approximately 60° C. under vacuum for 16 h to leave the title compound as a dense white solid (37.8 g, 83.7%).

Figure 3:
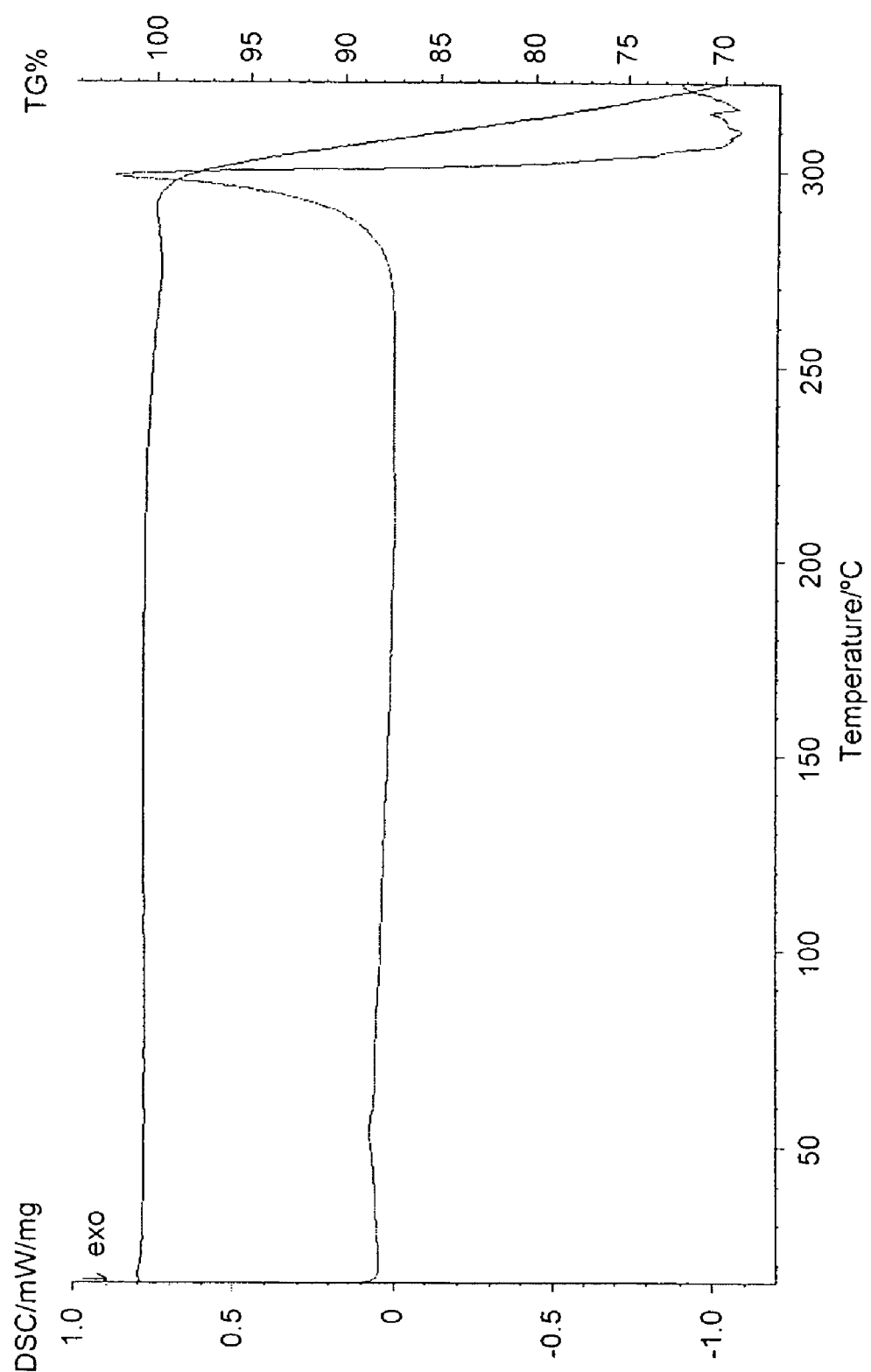
FIG. 3: DSC and TGA profiles of Form 1 polymorph of Unsolvated Compound of formula (I)

The XRPD pattern of Example 1 product is shown in FIG. 1. The DSC and TGA profiles are shown in FIG. 3.

Example 2

6α, 9α-Difluoro-17α-[(2-furanylcarbonyl)oxy]-11-hydroxy-16α-methyl-3-oxo-androsta-1,4-diene-17β-carbothioic Acid S-fluoromethyl Ester Unsolvated Form 2

A suspension of 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (prepared for example according to Example 1, first method) (6.0 g) in dichloromethane (180 ml) was heated to reflux giving a bright solution. The solution was clarified by hot filtration (Whatman 54 filter paper) and the solution was distilled at atmospheric pressure (approx 100 ml solvent collected) giving crystallisation at reflux. The mixture was held at reflux for approximately 30 minutes and slowly cooled to ambient temperature. The mixture was further cooled and aged at 10–20° C. for 2 hours. The slurry was cooled to below 10° C. and the product was filtered off, sucked dry and dried at approximately 60° C. under vacuum overnight to leave a white solid (4.34 g, 71%).

A more pure sample of 6α, 9α-difluoro-17α-[(2-furanylcarbonyl)oxy]-11β-hydroxy-16α-methyl-3-oxo-androsta-1, 4-diene-17β-carbothioic acid S-fluoromethyl ester unsolvated Form 2 was obtained by a cooling crystallisation of 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (prepared eg according to Example 1, first method) in methanol (60 volumes, distilled at atmospheric pressure to approx 37.5 volumes). The product was isolated by filtration and oven dried at 60° C. under vacuum for 16 hours to leave a white, electrostatic solid (4.34 g, 71%).

The XRPD pattern of Example 2 product is shown in FIG. 1.

Example 3

6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester Unsolvated Form 3

A suspension of 6α, 9α-difluoro-17α-[(2-furanylcarbonyl)oxy]-11β-hydroxy-16α-methyl-3-oxo-androsta-1,4-diene-17β-carbothioic acid S-fluoromethyl ester acetone solvate (prepared eg according to Example 11) (20.0 g) in dichloromethane (800 ml, 40 volumes) and water (10 ml, 0.5 volumes) was heated to reflux giving a bright solution. The solution was clarified by hot filtration (Whatman 54 filter paper) during which time some solid crystallised in the filtrate which was fully dissolved upon heating to reflux. The solution was distilled at atmospheric pressure (approx 400 ml solvent collected) and allowed to cool to ambient temperature. The mixture was further cooled and aged at <10° C. for 10 minutes. The product was filtered off, sucked dry and dried at approximately 60° C. under vacuum overnight to leave a white solid (12.7 g, 70%).

Figure 4:
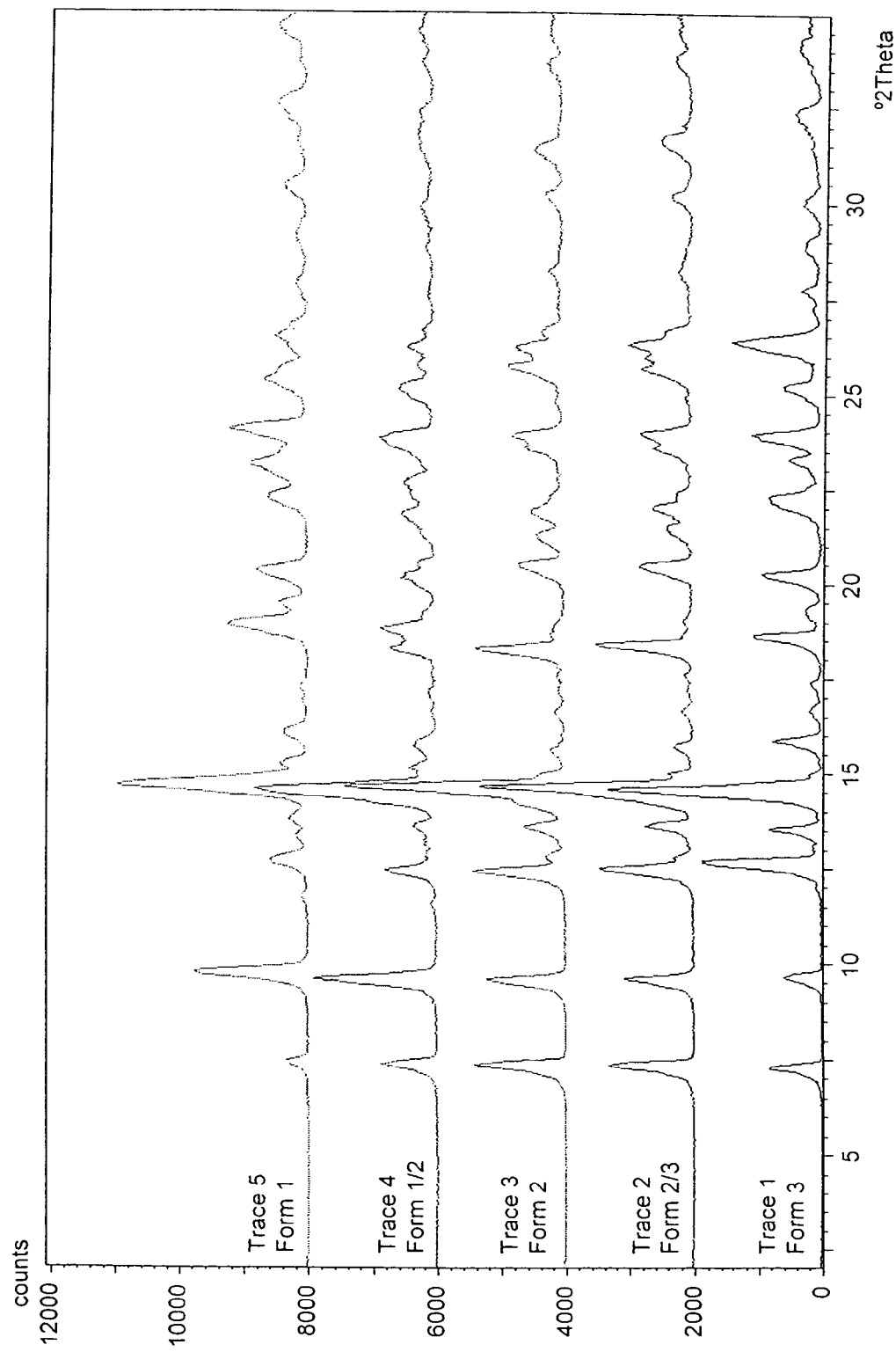
FIG. 4: Temperature dependence of the XRPD profile of Compound of formula (I) Unsolvated Form 3 obtained at 5 timepoints

The XRPD pattern of Example 3 product is shown in FIG. 1 and FIG. 4.

Example 4

Interconversion of Forms 1, 2 and 3 of unsolvated 6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester Slurrying a mixture of Form 1 and Form 2 in water at ambient temperature revealed that the components are transformed entirely to Form 1 with time.

XRPD results are shown in FIG. 2. Similar results were obtained by slurrying a mixture of Form 1 and Form 2 in ethanol at ambient temperature. From these results it may be concluded that Form 1 is the thermodynamically more stable polymorphic form out of the two forms.

Figure 5:
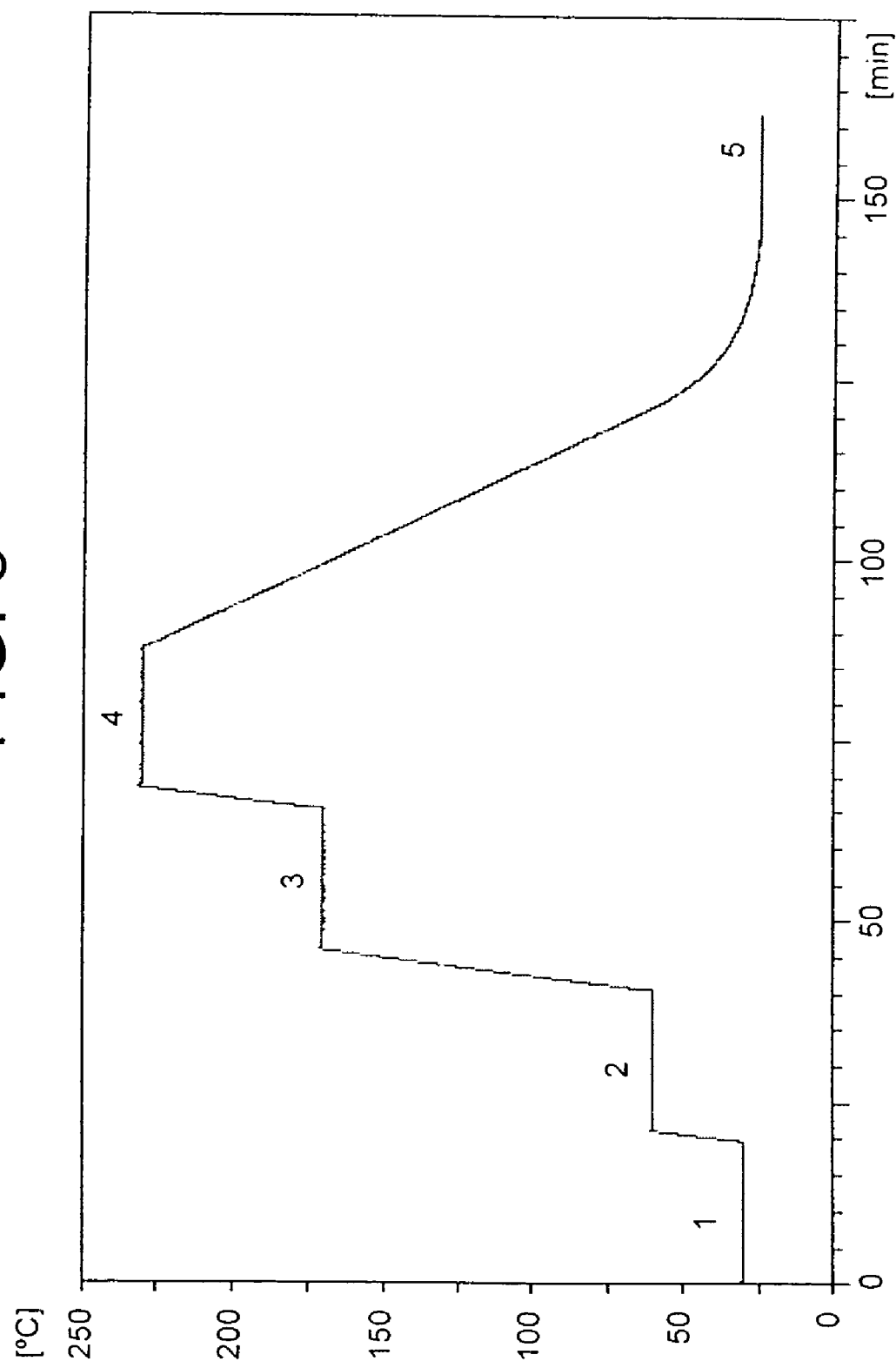
FIG. 5: Temperature and time profile for the XRPD experiments of FIG. 4

Thermal XRPD studies on Form 3 were performed as shown in FIG. 4. The temperature and time profile is shown in FIG. 5 and the 5 traces shown in FIG. 4 were obtained at the equilibration points shown in FIG. 5. The results indicate that Form 3 is converted first to Form 2 and then to Form 1 as temperature is elevated.

Example 5

Moisture Sorption of Forms 1, 2 and 3 of Unsolvated 6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester The moisture sorption characteristics of the three forms were determined by monitoring the weight change of solid when exposed to stepwise increased and then decreased humidity. The results obtained were as follows:

Form 1: uptake of 0.18% w/w of moisture over the range 0–90% relative humidity at 25° C.

Form 2: uptake of 1.1–2.4% w/w of moisture over the range 0–90% relative humidity at 25° C.

Form 3: uptake of 1.2–2.5% w/w of moisture over the range 0–90% relative humidity at 25° C.

Example 6

Enthalpy of Dissolution of Forms 1 and 3 of Unsolvated 6α, 9α-difluoro-17α-[(2-furanylcarbonyl)oxy]-11β-hydroxy-16α-methyl-3-oxo-androsta-1,4-diene-17β-carbothioic Acid S-fluoromethyl Ester Enthalpies of dissolution in DMSO and acetonitrile were determined at 25° C. The results were as follows:

|  | Form I | Form 3 |
| --- | --- | --- |
| Acetonitrile | +13.74 | +8.62 |
| DMSO | +1.46 | −5.21 |

(results in kJ/mol)

(results in kJ/mol)

Form these results it may be determined that the enthalpy of transition from Form 3 to Form 1 is approximately 5.1–6.7 kJ/mol. On the assumption that the entropy of transition is small, since both Forms are unsolvated, the enthalpy of transition may be equated with the free energy of transition. Thus these data suggest that Form 1 is the thermodynamically most stable form at 25° C.

Example 7

6α, 9α-Difluoro-17α-[(2-furanylcarbonyl)oxy]-11-hydroxy-16α-methyl-3-oxo-androsta-1,4-diene-17β-carbothioic Acid S-fluoromethyl Ester Methylethylketone Solvate A suspension of 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (prepared eg according to Example 1) (400 mg) in methylethylketone (3.2 ml) is heated to reflux giving a clear solution. A portion of the solvent is distilled off at atmospheric pressure (approx 1 ml) and the mixture cooled to approximately 20° C. The crystallised product is filtered off, dried at approximately 20° C. under vacuum to leave the title compound as a white solid (310 mg, 68%). NMR δ (CDCl$_3$) includes the peaks described in Example 1 for the parent compound and the following additional solvent peaks: 2.45 (2H, q), 2.14 (3H, s), 1.06 (3H, t).

Example 8

6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester Isopropanol Solvate A solution of 6α, 9α-difluoro-17α-[(2-furanylcarbonyl)oxy]-11α-hydroxy-16α-methyl-3-oxo-andros-1,4-diene-17β-carbothioic acid S-fluoromethyl ester (prepared eg according to Example 1) (150 mg) in isopropanol (15 ml) is left to slowly crystallise over a period of approximately 8 weeks. The resultant chunky crystals are isolated by filtration to leave the title compound as a white solid. NMR δ (CDCl$_3$) includes the peaks described in Example 1 for the parent compound and the following additional solvent peaks: 4.03 (1H, m), 1.20 (6H, d).

Example 9

6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester Tetrahydrofuran Solvate A suspension of 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (prepared eg according to Example 1) (150 mg) in THF (20 vol) is warmed to give a clear solution. The solvent is allowed to slowly evaporate over a period of 6 days to leave title compound as a white solid. Alternatively, the THF solution is added dropwise to solution of potassium bicarbonate (2% w/w) in water (50 vol) and the precipitated product collected by filtration to furnish the title compound as a white solid. NMR δ (CDCl$_3$) includes the peaks described in Example 1 for the parent compound and the following additional solvent peaks: 3.74 (4H, m), 1.85 (4H, m).

Example 9

6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester Tetrahydrofuran Solvate (Alternative Method)

A mobile suspension of 6α, 9α-difluoro-17α-[(2-furanylcarbonyl)oxy]-11β-hydroxy-16α-methyl-3-oxo-androsta-1,4-diene-17β-carbothioic acid-triethylamine salt (prepared eg according to Intermediate 1 B) (1.2 g) in THF (10 ml) is treated with a phase transfer catalyst (tetrabutylammonium bromide, typically between 8 and 14mol %), cooled to approximately 3° C. and treated with bromofluoromethane (0.98 equivalents). The suspension is stirred for between 2 and 5 hours, allowing to warm to 17° C. The reaction mixture is poured into water (30 vol), stirred at approximately 10° C. for 30 minutes and filtered off. The collected solid is washed with water (4×3 vol) and the product oven dried under vacuum at 60° C. overnight to give the title compound as a white solid (0.85 g, 87%).

Example 10

6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester DMF Solvate A mixture of Intermediate 1 (4.5 g, 8.88 mmol) in DMF (31 ml) is treated with potassium bicarbonate (0.89 g, 8.88 mmol) and the mixture is cooled to −20° C. A solution of bromofluoromethane (0.95 g, 8.50 mmol, 0.98 eqv.) in DMF (4.8 ml) at 0° C. is added and the mixture is stirred at −20° C. for 4 hours. The mixture is then stirred at −20° C. for a further 30 minutes, added to 2M hydrochloric acid (100 ml) and stirred for a further 30 minutes at 0–5° C. The precipitate collected by vacuum filtration, washed with water and dried at 50° C. to give the title compound (4.47 g, 82%). NMR δ (CD$_3$OD) includes the peaks described in Example 1 for the parent compound and the following additional solvent peaks: 7.98 (1 H, bs), 2.99 (3H, s), 2.86 (3H, s).

Example 11

6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester Acetone Solvate A solution of Intermediate 1 (530.1 g, 1 wt) in dimethylformamide (DMF) (8 vol) is treated with potassium hydrogen carbonate (0.202 wt, 1.02 eq) and the mixture cooled to −17±3° C. with stirring. Bromofluoromethane (BFM) (0.22 wt, O.99 eq) is then added and the reaction stirred at −17±3° C. for at least 2 h. The reaction mixture is then added to water (17 vol) at 5±3° C. over ca 10 min followed by a water (1 vol) line wash. The suspension is stirred at 5–10° C. for at least 30min and then filtered. The filter cake (the DMF solvate of 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester) is washed with water (4×4 vol) and the product is pulled dry on the filter. The damp cake is returned to the vessel, acetone (5.75 vol) added and heated at reflux for 2h. The mixture is cooled to 52±3° C. and water (5.75 vol) added, keeping temperature at 52±3° C. The mixture is then cooled to 20±3° C., filtered and dried in vacuo at 60±5° C. overnight to give the title compound as a white solid (556.5 g, 89%). NMR δ (CDCl$_3$) includes the peaks described in Example 1 for the parent compound and the following additional solvent peaks: 2.17 (6H, s).

Example 12

Dry Powder Composition Containing 6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester, Unsolvated Form 1

A dry powder formulation was prepared as follows:

| | |
|---|---|
| 6α,9α-Difluoro-17α-[(2-furanylcarbonyl)oxy]-11β-hydroxy-16α-methyl-3-oxo-androsta-1,4-diene-17β-carbothioic acid | 0.20 mg |

-continued

| A dry powder formulation was prepared as follows: | |
|---|---|
| S-fluoromethyl ester, unsolvated Form 1 (prepared according to Example 1, first alternative method and micronised to a MMD of 3 μm): | |
| milled lactose (wherein not greater than 85% of particles have a MMD of 60–90 μm, and not less than 15% of particles have a MMD of less than 15 μm): | 12 mg |

A peelable blister strip containing 60 blisters each filled with a formulation as just described was prepared.

Example 13

Aerosol Formulation Containing 6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester, Unsolvated Form 1

| An aluminium canister was filled with a formulation as follows: | |
|---|---|
| 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, Unsolvated Form 1 (prepared according to Example 1, first alternative method) and micronised to a MMD of 3 μm): | 250 μg |
| 1,1,1,2-tetrafluoroethane: (amounts per actuation) in a total amount suitable for 120 actuations and the canister was fitted with a metering valve adapted to dispense 50 μl per actuation. | to 50 μl |

Example 14

Nasal Formulation Containing 6α, 9α-Difluoro-17α-[(2-furanylcarbonyl)oxy]-11β-hydroxy-16α-methyl-3-oxo-androsta-1,4-diene-17β-carbothioic Acid S-fluoromethyl Ester, Unsolvated Form 1

| A formulation for intranasal delivery was prepared as follows: | |
|---|---|
| 6α,9α-Difluoro-17α-[(2-furanylcarbonyl)oxy]-11β-hydroxy-16α-methyl-3-oxo-androsta-1,4-diene-17β-carbothioic acid S-fluoromethyl ester Unsolvated Form 1 (prepared according to Example 1, first alternative method, micronised): | 10 mg |
| Polysorbate 20 | 0.8 mg |
| Sorbitan monolaurate | 0.09 mg |
| Sodium dihydrogen phosphate dihydrate | 94 mg |
| Dibasic sodium phosphate anhydrous | 17.5 mg |
| Sodium chloride | 48 mg |
| Demineralised water | to 10 ml |

The formulation was fitted into a spraypump capable of delivering a plurality of metered doses (Valois).

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The patents and patent applications described in this application are herein incorporated by reference.

The invention claimed is:

1. A compound of formula (X):

(X)